(12) United States Patent
Skovgaard et al.

(10) Patent No.: US 12,396,890 B2
(45) Date of Patent: Aug. 26, 2025

(54) APPARATUS FOR PHOTOTHERMAL OPHTHALMIC TREATMENT

(71) Applicant: Norlase ApS, Ballerup (DK)

(72) Inventors: Peter Skovgaard, Birkerød (DK); Greg Fava, Redwood City, CA (US)

(73) Assignee: Norlase ApS, Ballerup (DK)

( * ) Notice: Subject to any disclaimer, the term of this patent is extended or adjusted under 35 U.S.C. 154(b) by 0 days.

(21) Appl. No.: 16/484,575

(22) PCT Filed: Feb. 6, 2018

(86) PCT No.: PCT/EP2018/052896
§ 371 (c)(1),
(2) Date: Aug. 8, 2019

(87) PCT Pub. No.: WO2018/146070
PCT Pub. Date: Aug. 16, 2018

(65) Prior Publication Data
US 2019/0365569 A1     Dec. 5, 2019

Related U.S. Application Data

(60) Provisional application No. 62/456,829, filed on Feb. 9, 2017.

(30) Foreign Application Priority Data

Sep. 11, 2017   (DK) .............................. PA201770679

(51) Int. Cl.
*A61F 9/008*     (2006.01)
*A61B 17/00*     (2006.01)
(Continued)

(52) U.S. Cl.
CPC ........ *A61F 9/00823* (2013.01); *A61N 5/0625* (2013.01); *G10L 15/22* (2013.01);
(Continued)

(58) Field of Classification Search
CPC .............. A61F 9/00823; A61F 9/00821; A61F 2009/00863; A61F 2009/00891;
(Continued)

(56) References Cited

U.S. PATENT DOCUMENTS

| 4,164,222 A | 8/1979 | Prokhorov et al. |
| 4,638,801 A | 1/1987 | Daly et al. |

(Continued)

FOREIGN PATENT DOCUMENTS

| EP | 1584310 | 10/2005 |
| EP | 1377243 | 1/2011 |

(Continued)

OTHER PUBLICATIONS

"Slit lamp," 2016, Wikipedia. Retrieved from: https://web.archive.org/web/20160914003932/https://en.wikipedia.org/wiki/Slit_lamp. (Year: 2016).*

(Continued)

*Primary Examiner* — Michael W Kahelin
*Assistant Examiner* — Luke M Stanley
(74) *Attorney, Agent, or Firm* — ICE MILLER LLP; Justin D. Swindells

(57) ABSTRACT

An apparatus for photothermal ophthalmic treatment, in particular photocoagulation or photo-thermal stimulation, the apparatus comprising a diagnostic instrument and an adapter unit, the diagnostic instrument being configured to emit illumination light from an illumination output along a free-air illumination output path towards a target area, to receive light from the target area along a free-air viewing path and to provide a magnified view of the target area, wherein the adapter unit comprises: a housing detachably mountable to said diagnostic instrument; at least one treatment direct diode laser positioned within the housing; the direct diode laser comprising a treatment laser diode con- (Continued)

figured to emit light at a wavelength suitable for photothermal ophthalmic treatment in the wavelength range of 480 and 632 nm, one or more optical elements configured to direct the emitted light as a treatment light beam towards the target area when the housing is mounted to said diagnostic instrument; and wherein the treatment direct diode laser is located above or in line with said viewing path when the housing is mounted to said diagnostic instrument and wherein at least one of the optical elements is configured to extend into at least one of the free-air viewing path and the free-air illumination output path of the diagnostic instrument when the housing is mounted to said diagnostic instrument in an operational position.

26 Claims, 8 Drawing Sheets

(51) Int. Cl.
A61N 5/06 (2006.01)
G10L 15/22 (2006.01)
A61B 3/16 (2006.01)
A61B 18/00 (2006.01)

(52) U.S. Cl.
CPC ....... A61B 3/16 (2013.01); A61B 2017/00115 (2013.01); A61B 2017/00203 (2013.01); A61B 2017/00221 (2013.01); A61B 2017/00734 (2013.01); A61B 2018/00702 (2013.01); A61F 2009/00863 (2013.01); A61F 2009/00891 (2013.01); A61N 2005/0626 (2013.01); A61N 2005/0663 (2013.01); G10L 2015/223 (2013.01); G10L 2015/225 (2013.01)

(58) Field of Classification Search
CPC ........ A61F 2009/00868; A61N 5/0625; A61N 2005/0626; A61N 2005/0663; G10L 2015/223; G10L 2015/225; G10L 15/22; A61B 2017/00203; A61B 2017/00221; A61B 2017/00734; A61B 2017/00115; A61B 3/16; A61B 2018/00702; A61B 90/20

See application file for complete search history.

(56) References Cited

U.S. PATENT DOCUMENTS

| | | | |
|---|---|---|---|
| 4,694,290 A | 9/1987 | Schwarz | |
| 4,917,486 A | 4/1990 | Raven et al. | |
| 5,147,349 A | 9/1992 | Johnson et al. | |
| 5,300,062 A * | 4/1994 | Ueno | A61F 9/00821 606/4 |
| 5,413,555 A * | 5/1995 | McMahan | A61F 9/008 606/4 |
| 5,634,923 A * | 6/1997 | Brenner | G02B 5/22 606/4 |
| 5,954,711 A * | 9/1999 | Ozaki | A61F 9/008 606/6 |
| 6,370,168 B1 | 4/2002 | Spinelli | |
| 6,383,178 B1 * | 5/2002 | Abe | A61F 9/00821 606/2 |
| 6,454,761 B1 * | 9/2002 | Freedman | A61F 9/00804 600/407 |
| 7,921,017 B2 | 4/2011 | Claus et al. | |
| 11,094,321 B2 | 8/2021 | Fava et al. | |
| 2002/0133145 A1 * | 9/2002 | Gerlach | G02B 21/06 606/4 |
| 2003/0208189 A1 | 11/2003 | Payman | |
| 2004/0057119 A1 * | 3/2004 | Sagehashi | A61F 9/00821 359/618 |
| 2004/0078029 A1 | 4/2004 | Momiuchi et al. | |
| 2005/0026745 A1 | 2/2005 | Mitrovic | |
| 2005/0267450 A1 * | 12/2005 | Harumoto | A61F 9/008 606/4 |
| 2006/0161145 A1 | 7/2006 | Lin et al. | |
| 2008/0015553 A1 | 1/2008 | Zacharias | |
| 2008/0021711 A1 | 1/2008 | Claus et al. | |
| 2011/0098692 A1 * | 4/2011 | Shazly | A61F 9/008 606/10 |
| 2011/0199579 A1 * | 8/2011 | Muto | A61B 3/14 351/208 |
| 2011/0228803 A1 | 9/2011 | Guenter et al. | |
| 2011/0246165 A1 | 10/2011 | Dai et al. | |
| 2012/0191078 A1 | 7/2012 | Yadlowsky et al. | |
| 2013/0085481 A1 * | 4/2013 | Dick | A61F 9/00823 606/4 |
| 2013/0128223 A1 | 5/2013 | Wood et al. | |
| 2013/0253411 A1 | 9/2013 | Rubinchik et al. | |
| 2014/0058367 A1 * | 2/2014 | Dantus | H01S 3/005 606/4 |
| 2014/0081248 A1 | 3/2014 | Blumenkranz et al. | |
| 2015/0202083 A1 * | 7/2015 | Takeda | A61F 9/009 606/4 |
| 2015/0265464 A1 | 9/2015 | Beder et al. | |
| 2015/0290031 A1 * | 10/2015 | Wellhoefer | G06F 3/03 345/156 |
| 2015/0366713 A1 * | 12/2015 | Shazly | A61F 9/00821 606/5 |
| 2016/0270656 A1 * | 9/2016 | Samec | A61B 3/1015 |
| 2016/0346126 A1 | 12/2016 | Luttrull et al. | |
| 2017/0112572 A1 * | 4/2017 | Shazly | A61B 18/20 |
| 2017/0189228 A1 * | 7/2017 | Yang | A61B 3/102 |
| 2017/0209307 A1 | 7/2017 | Liesfeld et al. | |
| 2017/0304018 A1 * | 10/2017 | Papac | A61F 9/00736 |
| 2020/0405540 A1 * | 12/2020 | Flanders | A61F 9/00814 |

FOREIGN PATENT DOCUMENTS

| | | | |
|---|---|---|---|
| JP | H 05500315 A | 1/1993 | |
| JP | H 07194645 A | 8/1995 | |
| JP | 2014534011 A | 12/2014 | |
| WO | WO 91001703 | 2/1991 | |
| WO | WO 02083041 | 10/2002 | |
| WO | WO 2007127257 | 11/2007 | |
| WO | WO 2008106590 | 9/2008 | |
| WO | WO-2012155929 A1 * | 11/2012 | ............... A61B 3/10 |
| WO | WO2013/059564 A1 * | 4/2013 | ............... A61B 3/10 |
| WO | WO 2013059564 | 4/2013 | |
| WO | WO 2014070119 | 5/2014 | |
| WO | WO 2014183792 | 11/2014 | |
| WO | WO 2015170947 | 11/2015 | |
| WO | WO 2016154589 | 9/2016 | |
| WO | WO 2017122061 | 7/2017 | |

OTHER PUBLICATIONS

Masui, S., et al., "1 W AlInGaN Based Green Laser Diodes," Conference on Lasers and Electro-Optic Pacific Rim (CLEO-PR), 1-2 (2013).
Masui, S., et al., "Recent Improvement in Nitride Lasers," Proc. of SPIE, 10104: 101041H-1-101041H-8 (2017).
Willstrand, O., "Intensity Distribution Conversion from Gaussian to Top-Hat in a Single-Mode Fiber Connector," Lund University, 1-53 (2013).
International Preliminary Report on Patentability, mailed on Aug. 22, 2019, from International Application No. PCT/EP2018/052896, filed on Feb. 6, 2018. 14 pages.
Becker, B.C., et al. "Semiautomated Intraocular Laser Surgery Using Handheld Instruments," Lasers in Surgery and Medicine, 42: 264-273 (2010).
International Search Report and Written Opinion of the International Searching Authority, mailed on Sep. 24, 2018, from International Application No. PCT/EP2018/052896, filed on Feb. 6, 2018. 18 pages.
Yang, S., et al., "Handheld Automated Microsurgical Instrumentation for Intraocular Laser Surgery," Lasers Surg. Med., 47(8): 658-668 (2015).

(56) References Cited

OTHER PUBLICATIONS

Extended European Search Report, dated on Jan. 22, 2020, from European Application No. 19196932.8, filed on Sep. 12, 2019. 7 pages.
Partial International Search Report of the International Searching Authority, mailed on Jun. 11, 2018, from International Application No. PCT/EP2018/052896, filed on Feb. 6, 2018. 10 pages.
Japanese Search Report searched Nov. 11, 2021, from Japanese Patent Application No. 2019-543108, filed on Feb. 6, 2018. 26 pages.
Extended European Search Report issued in EP Application No. 24211039.3, dated Jan. 27, 2025 [17 Pages].

\* cited by examiner

APPARATUS FOR PHOTOTHERMAL OPHTHALMIC TREATMENT

RELATED APPLICATIONS

This application is a § 371 National Phase Application of International Application No. PCT/EP2018/052896, filed on Feb. 6, 2018, now International Publication No. WO 2018/146070, published on Aug. 16, 2018, which International Application claims the benefit under 35 USC 119 (e) of U.S. Provisional Application No. 62/456,829, filed on Feb. 9, 2017, and which International Application claims priority to Danish Application No. PA201770679, filed on Sep. 11, 2017, all of which are incorporated herein by reference in their entirety.

FIELD OF THE INVENTION

The present invention relates to an apparatus for photothermal ophthalmic treatment by causing absorption of light by structures of a subject's eye, such as melanin or blood, in particular for photocoagulation or photo-thermal stimulation to treat retina and glaucoma disease, and, in particular, an medical laser apparatus for emitting therapeutic light for ophthalmic treatment.

BACKGROUND

Lasers are extensively used in the medical field for surgery, such as ophthalmic surgical systems, e.g. as described in U.S. Pat. No. 5,147,349, US 2011/0098692 and US 2004/0078029.

For the laser sources, a number of technologies are known, including infrared laser diodes, e.g. as described in U.S. Pat. No. 4,917,486. Recently, optically pumped semiconductor lasers, e.g. as described in U.S. Pat. No. 6,370,168, have been widely adopted by manufacturers of for example photocoagulation or photo-thermal stimulation systems. Such systems are used at large medical centers, hospitals and individual offices. In addition, various techniques are today being explored to automate the surgery procedures, see for example Becker, B. C., MacLachlan, R. A., Lobes, L. A. and Riviere, C. N. (2010), Semiautomated intraocular laser surgery using handheld instruments. Lasers Surg. Med., 42: 264-273. doi: 10.1002/lsm.20897. Other works are performed by Yang, S., Lobes, L. A., Martel, J. N. and Riviere, C. N. (2015), Handheld-automated microsurgical instrumentation for intraocular laser surgery. Lasers Surg. Med., 47: 658-668. doi: 10.1002/lsm.22383). Despite these efforts, deployment of ophthalmic surgical systems, including photocoagulation or photo-thermal stimulation lasers, at point-of-care level is largely absent.

Photothermal therapy, such as photocoagulation or photothermal stimulation, requires sufficiently high output powers so as to allow the structures of the eye to absorb sufficient energy at a selected, well-defined target site within short period of times.

US 2005/0267450 discloses an ophthalmic treatment apparatus where a light source unit with a semiconductor pumped solid-state laser is attached to a main body of the apparatus with a bayonetted coupling. The light beam from the semiconductor pumped solid-state laser enters the main body of the ophthalmic treatment apparatus and is introduced into the internal optical path of the apparatus. While this solution avoids the need for an external fibre-optic cable, it is a rather bulky, complex and costly solution that requires a dedicated and customized ophthalmic treatment apparatus with a special interface for introducing a laser beam into the main body of the apparatus.

In this context it is generally desirable to provide an apparatus for ophthalmic treatment with improved ease of use for the operator.

It is further generally desirable to provide an apparatus for ophthalmic treatment that can be manufactured in a cost-efficient manner.

It is further generally desirable to provide a compact and versatile solution.

It is further generally desirable to reduce the complexity of existing solutions.

It is further generally desirable to provide an apparatus for ophthalmic treatment that are durable.

SUMMARY

According to a first aspect, disclosed herein is an apparatus for photothermal ophthalmic treatment, in particular photocoagulation or photo-thermal stimulation, and, in particular, an apparatus for emitting therapeutic laser light for ophthalmic treatment and a diagnostic instrument adapter unit being in direct physical contact with said diagnostic instrument, hereafter also referred to as an "adapter unit". The diagnostic instrument is configured to emit illumination light from an illumination output along a free-air illumination output path towards a target area for ophthalmic treatment. The diagnostic instrument is further configured to receive light from the target area along a free-air viewing path and to provide a magnified view of the target area. The adapter unit comprises:

- a housing detachably mountable to said diagnostic instrument;
- at least one treatment direct diode laser positioned within the housing; the direct diode laser comprising a treatment laser diode configured to emit light at a wavelength suitable for photothermal ophthalmic treatment in the wavelength range of 480 and 632 nm,
- one or more optical elements configured to direct the emitted light as a treatment light beam towards the target area when the housing is mounted to said diagnostic instrument; wherein the treatment direct diode laser is located above or in line with said viewing path when the housing is mounted to said diagnostic instrument and wherein at least one of the optical elements is configured to extend into at least one of the free-air viewing path and the free-air illumination output path of the diagnostic instrument when the housing is mounted to said diagnostic instrument in an operational position.

The present disclosure also relates to an adapter unit for such an apparatus for ophthalmic treatment.

It is an advantage of a direct diode laser that it has low power consumption and generates sufficiently little heat to allow being accommodated in the adapter unit. The, or each, treatment laser diode is a monolithic device, i.e. an optical system integrated together in a single integrated circuit that is operable to directly emit laser light suitable for photothermal ophthalmic treatment at a wavelength between 480 nm and 632 nm, in particular light in the green and/or yellow visible range, thus providing a compact design and allowing the housing to be made particularly light weight and small. This allows the housing to be directly, preferably movably, mounted to the diagnostic instrument. Generally, the treatment direct diode laser receives and is powered by electrical power and emits therapeutic light. It has turned out that an adapter unit with a direct diode laser source requires 5-10 times less cooling than a unit comprising a semiconductor pumped solid-state laser. Moreover, an adapter unit with a direct diode laser source can be made considerably more compact and is significantly less complex to control and operate.

As the adapter unit is mounted to the diagnostic instrument above or in line with the viewing path of the diagnostic instrument, a compact design of the apparatus for ophthalmic treatment is provided; the adapter unit can be retrofit to existing diagnostic instruments without interfering with other parts of the instrument. Moreover, the apparatus for ophthalmic treatment does not require an external fiber-optic connection between the adapter unit and an external treatment light source. As the adapter unit introduces the treatment light beam into the free-air illumination output path and/or the free-air viewing path of the diagnostic instrument, no part of the treatment light beam needs to enter any housing or internal optical path of the diagnostic instrument, thus allowing easy retrofit of the adapter unit to conventional diagnostic instruments.

The adapter unit with integrated treatment direct diode laser may be manufactured at relatively low manufacturing costs and can be retrofitted to existing diagnostic instruments. In particular, mounting the adapter unit with the treatment direct diode laser above or in line with the viewing path where the treatment light beam is introduced along the free-air illumination output path and/or the free-air viewing path of the diagnostic instrument allows mounting of the adapter unit to a variety of different types of diagnostic instruments without the adapter unit interfering with other components of the diagnostic instrument and without need for constructional modifications to the diagnostic instrument.

Embodiments of the adapter unit are mounted directly to the diagnostic instrument above or in line with the viewing path and they include:
   a treatment direct diode laser source that emits light, and
   optical elements which direct the emitted light as a treatment light beam towards the target area that is illuminated by the illumination light from the diagnostic instrument.

Hence, the operator does not need to operate a space-consuming remote treatment light source connected to the apparatus via fiber-optical cable but can still easily attach the adapter unit to conventional existing diagnostic systems. This provides an advantage in terms of ease-of-use to the operator. A further advantage of this is a reduced risk of error by accidental incidents to the remote light source and/or fiber-optical cable—hence, a safer more reliable surgical operation. Generally an operator of embodiments of an apparatus described herein may be a physician, medical doctor, surgeon or similar health professional.

Embodiments of a diagnostic instrument generally comprise an illumination light source and one or more optical elements, e.g. one or more lenses and/or one or more mirrors and/or one or more beam splitters and/or the like, for directing light from the illumination light source towards a target area along the illumination output path. The diagnostic instrument may direct the illumination light towards an illumination output of the diagnostic instrument along an internal illumination path from the illumination light source to the illumination output. The internal illumination path may comprise multiple path segments e.g. multiple straight path segments extending between suitable optical elements for redirecting the illumination light beam.

Embodiments of a diagnostic instrument further comprise one or more optical elements, e.g. one or more lenses and/or one or more mirrors and/or one or more beam splitters and/or a microscope and/or a zoom telescope and/or the like, configured to provide a magnified view of one or more portions of a subject's eye and, in particular, of the illuminated target area, along the viewing path. The optical elements of the diagnostic instrument may be configured such that the illumination output path and the viewing path intersect within the target area and/or are focused at the target area. In particular, embodiments of a diagnostic instrument generally comprise a magnifying optical device, such as a microscope or zoom telescope, for providing a magnified view of the target area from which light is received along the viewing path. The diagnostic instrument may comprise one or more oculars for directly observing the magnified view, or an image capturing device, such as a camera, for capturing an image of the magnified view. Alternatively or additionally, the diagnostic instrument may comprise an interface for such oculars and/or for an image capturing device. The magnifying optical device is typically accommodated within a viewer housing of the diagnostic instrument. In some embodiments, the treatment direct diode laser is positioned above, or at the same height as, the viewer housing, e.g. mounted to a mounting platform accommodated at the viewer housing, e.g. at an upper surface of the viewer housing.

In some embodiments, the diagnostic instrument is a slit lamp or an operating microscope, i.e. the adapter unit may be a slit lamp adapter unit or an adapter unit for an operating microscope.

Generally, the term slit lamp refers to a diagnostic tool operable to provide a magnified view of the anterior and/or posterior portions of a subject's eye. It may be regarded as a microscope that can provide different magnified views and, with the addition of either a contact or non-contact lens, can allow a view of the retina or other portions of the eye that may require diagnosis or treatment. The name "slit lamp" refers to the white light illumination provided by a slit lamp as this illumination is often mechanically attenuated into a "slit" of illumination at the targeted region. This slit illumination reduces back scatter, reflections and is more comfortable for the patients to tolerate. However, for the purpose of the present description, the term slit lamp also refers to such devices that do not comprise a slit.

The illumination output path extends from an illumination output of the diagnostic instrument towards the target, i.e. the term illumination output path is intended to refer to the free-air path of the illumination light between the illumination output where the illumination light exits the diagnostic instrument and the location where the illumination light enters the target. The illumination output may be defined by an optical element of the diagnostic instrument, such as a lens, an aperture, a mirror, etc. and, in particular by the last optical element of an optical train of elements that defines the illumination path of the diagnostic instrument.

Similarly, the viewing path extends from the target area to a viewing input of the diagnostic instrument, i.e. the term viewing path is intended to refer to the free-air axis along which the diagnostic instrument receives the light from the target area for providing a magnified view of the target area; the viewing path extends from the target area to the viewing input of the diagnostic instrument. The viewing input may be defined by an optical element of the diagnostic instrument, such as a lens, an aperture, a mirror, etc. and, in particular by the first optical element of the magnifying optical device that receives the incoming light. The optical element of the adapter element (e.g. a dichroic mirror) from which the treatment light beam is directed to the target area is positioned between the target area and the viewing input of the diagnostic instrument.

As at least a part of the adapter unit including the treatment direct diode laser is located above or in line with the viewing path, the adapter unit is located above or in line with the viewing input of the diagnostic instrument. Here the term "above the viewing path" is intended to refer to a position higher than the viewing path when the diagnostic instrument is in use, irrespective of whether the adapter unit is located directly above, i.e. in vertical alignment with, the viewing path or whether it is horizontally displaced from the viewing path. The term "in line with the viewing path" is intended to refer to a position aligned with the viewing path.

In some embodiments, the treatment direct diode laser is also positioned above or in line with the illumination output path. In particular, in some embodiments, the viewing path and the illumination output path may be at the same height. Generally, the illumination output path and the viewing path may coincide (e.g. intersect) with each other at least at the target area, i.e. at the target tissue in the subject's eye to be treated. The illumination light and/or the viewing optics may be focused at the target area.

Common types of diagnostic slit lamps include two types that are commonly referred to as either "Zeiss Style" or "Haag-Streit style" design, respectively. In both types of slit lamps the illumination output path and the viewing path are typically substantially horizontal. In "Zeiss style" slit lamps the illumination source is located below the illumination output path and lower than the viewing path. The illumination light is thus upwardly directed from the illumination light source to one or more mirrors or the like which redirect(s) the illumination light towards the target area along the illumination output path. Zeiss-style slit lamps are also referred to as "bottom illumination style" slit lamps. In "Haag-Streit style" slit lamps the illumination light source is located above the illumination output path and above the viewing path. The illumination light is thus downwardly directed from the illumination source to one or more mirror(s) or the like which redirects the illumination light towards the target area along the illumination output path. Haag-Streit style slit lamps are also referred to as "top illumination style" slit lamps. Embodiments of the adapter unit described herein may be retrofitted to both types and, optionally, to other types of slit lamps.

Operating microscopes are often configured to output illumination light along a downwardly directed illumination output path towards a subject lying on the subject's back facing upwards. Similarly, operating microscopes are often configured to receive light along an upwardly directed viewing path from a subject lying on the subject's back facing upwards. A position above or in line with the viewing path is thus a position above or in line with the viewing input, i.e. the entry point of the light, into the operating microscope.

Generally, the treatment direct diode laser may be located above, or in line with the entire optical path between the target area and an ocular through which the operator can observe the magnified view of the target area (or an image capturing device configured to capture the magnified image of the target area). In particular, the treatment direct diode laser may be located above or in line with the magnifying optical device of the diagnostic instrument.

In some embodiments, the housing is movably mountable to the diagnostic instrument such that it can be moved, e.g. swiveled, slid or pivoted, relative to the viewing path. In some embodiments, the housing may selectively be moveable between an operational position (such that the treatment light beam is directed towards the target area when the adapter unit is at its operational position) and a parking position. When the diagnostic instrument is to be used without treatment light beam, the housing can thus be moved out of the way into the parking position without having to detach the housing from the diagnostic instrument.

The housing may comprise a mounting element and the diagnostic instrument may comprise a mounting platform at a mounting position where the mounting position may be located above or in line with the viewing path. The mounting element may be configured to engage with the mounting platform for detachable attachment of the housing. When mounted to the diagnostic instrument, the mounting element of the housing may thus engage the mounting platform in direct physical contact or via an adapter element. The mounting platform may comprise a tonometer mount or a dovetail mount or any other suitable mounting platform to which the mounting element of the housing can be attached by a screw, a snap connector, latching connector, bayonet connector or any other suitable type of cooperating mounting members. Many existing slit lamps comprise a mounting platform, called a "tonometer mount", operable to mount various exterior devices needed for diagnosis or treatment within ophthalmology. When the adapter unit comprises a mounting element configured to detachably engage a tonometer mount, a particularly expedient retrofit of the adapter unit to existing slit lamps is facilitated. Preferably the adapter unit may selectively be retrofit to both Haag-Streit style and Zeiss-style slit lamps.

The mounting element and/or the housing of the adapter unit may be configured such that the entire housing, or at least a major part of the housing, such as at least 50% of the volume of the housing, e.g. at least 75%, such as at least 90% of the volume of the housing, is located above the viewing path when the housing is mounted to the diagnostic instrument and when the adapter unit is in its operation position.

The treatment laser diode may be a single-mode or a multimode treatment laser diode. The treatment laser diode is configured to directly emit laser light at a wavelength suitable for ophthalmic treatment, i.e. without the need for further components for frequency conversion, for other lasers pumped by the diode, or the like. This allows the dimensions of the housing and the weight of the adapter unit to be further reduced as the need for frequency converters is avoided. This, in turn, facilitates mounting, in particularly movably mounting, of the adapter unit to the diagnostic instrument above or in line with the viewing path of the diagnostic instrument without unduly interfering with other components of the diagnostic instrument. In particular the compact housing and the mounting at the mounting position above or in line with the viewing path allows an operator of the system free access to the relevant parts of the system, such as the table top, which is also the base for the slit lamp. Moreover, space for a remote treatment light source is not required.

Preferably, the single mode or multimode treatment laser diode is a green treatment laser diode, for example a green treatment laser diode emitting light in the range between 500 nm and 570 nm, such as between 510 nm and 540 nm, such as between 510 nm and 530 nm, such as at 532 nm or at 520 nm, preferably with a maximum power of 1000 mW or more. Examples of such a green treatment laser diode that are currently available include the laser diode 'NDG7K75T' available from Nichia Corporation, Japan and the LDM-520-1000-A laser diode available from Lasertack GmbH. However, other direct diode lasers may be used as well, e.g.

laser diodes emitting laser light in the yellow range in the range between 570 nm and 590 nm, such as at 577 nm, preferably with a maximum power of 1000 mW or more.

The treatment light beam has an intensity and wavelength suitable for photothermal ophthalmic treatment of a subject's eye, in particular suitable for therapeutic ophthalmic treatment, such as photocoagulation or photo-thermal stimulation, e.g. so as to treat retina and glaucoma disease. Wavelengths suitable for photothermal ophthalmic treatment generally comprise visible and/or near-infrared wavelengths such as in the range between 400 nm and 850 nm. In particular, the treatment light beam has have a wavelength in the range from 480 nm to 632 nm, such as from 500 nm to 600 nm, such as from 510 nm to 580 nm, such as from 510 nm to 540 nm, such as from 510 nm to 530 nm, such as from 510 nm to 525 nm, such as at 532 nm or at 520 nm, or such as from 530 nm to 580 nm, such as at 532 nm, at 561 nm or at 577 nm. It is thus preferred that the light emitted by the treatment laser diode has a wavelength in the range from 480 nm to 632 nm, such as from 500 nm to 600 nm, such as from 510 nm to 580 nm, such as from 510 nm to 540 nm, such as from 510 nm to 530 nm, such as from 510 nm to 525 nm, such as at 520 nm or at 532 nm, or such as from 530 nm to 580 nm, such as at 532 nm, at 561 nm or at 577 nm. The wavelength of the treatment laser diode is normally expressed as its center wavelength. It will be appreciated that the treatment laser diode may generally emit light in a small wavelength range around its center wavelength e.g. within +/−3 nm around its center wavelength.

In some embodiments, the direct diode laser has an average power of less than 100 mW. In other embodiments, the treatment direct diode laser has an average power of more than 100 mW, such as more than 200 mW, such as more than 300 mW, such as more than 400 mW, and less than 3000 mW, such as less than 2000 mW, such as less than 1500 mW, such as less than 1000 mW, such as less than 500 mW. In other embodiments, the treatment direct diode laser has an average power between 300-1000 mW. Accordingly, the treatment laser diode may have an average power of more than 100 mW, such as more than 200 mW, such as more than 300 mW, such as more than 400 mW, and less than 3000 mW, such as less than 2000 mW, such as less than 1500 mW, such as less than 1000 mW, such as less than 500 mW. In other embodiments, the treatment laser diode has an average power between 300-1000 mW.

In some embodiments, the treatment light beam has a power in the range from 30 mW to 3000 mW, such as from 30 mW to 2000 mW, such as from 200 mW to 500 mW, such as from 300 mW to 1000 mW, such as from 400 mW to 2000 mW. It is preferable that the apparatus is configured to allow the power of the treatment light beam to be adjusted such that the treatment light beam may be adjusted to a user-selectable power up to a maximum power, e.g. up to a maximum power of at least 1 W, preferably at least 1.5 W, more preferably more than 1.5 W.

In some embodiments, the one or more optical elements of the adapter unit comprise one or more elements chosen from a lens, a beam shaper or a beam homogenizer for adjusting a beam profile of the emitted light. In some embodiments, the one or more optical elements are configured to direct the treatment light beam from an output of the adapter unit in free space towards the target area, in particular such that the beam path of the treatment light beam coincides (e.g. intersects) with the viewing path and, preferably, with the illumination output path at least at the target area. The treatment light beam may be focussed at the target area. The treatment light beam may be directed coaxially with, parallel to, or at an angle relative to the viewing path.

The optical elements of the adapter unit may comprise an optical element such as a mirror, e.g. a dichroic mirror, e.g. as a last element of an optical train of optical elements, for directing the treatment light beam of the adapter unit towards the target area, such that the treatment light beam coincides (e.g. intersects) with the viewing path and, preferably, with the illumination output path at least at the target area. The adapter unit is configured such that, when the adapter unit is mounted to the diagnostic instrument, e.g. via a tonometer mount, and at least when brought into its operational position, the mirror extends into the free-air viewing path and/or the free-air illumination path of the diagnostic instrument, i.e. the beam path of the adapter unit does not have to enter any housing and internal beam paths of the diagnostic instruments, thereby allowing the adapter unit to be retrofit to conventional diagnostic instruments.

In some embodiments, the one or more optical elements comprise beam shaping optics configured to homogenize said light.

In some embodiments, the optical elements are configured to shape the treatment beam such that it has a spot size (diameter) in a free space (i.e. in air) focal plane of between 50 μm and 500 μm, thus allowing for selective and efficient photothermal treatment. One or more of the optical elements may be adjustable so as to allow user-operated spot size selection e.g. in the range between 50 μm and 500 μm.

In some embodiments, the adapter unit is configured to provide the treatment laser beam as a pulsed beam where the pulse width is between 10 μs and 1 s. For example, the pulsed beam may be in the form of micro-pulses providing pulse envelopes having a duration/width between 10 ms and 1 s. In other embodiments without micro-pulsing, the pulses may have a width between 10 ms and 1 s. Preferably, the pulse width is user-selectable. Preferably, also the interval between consecutive pulses, i.e. the repeat interval, is user-controllable.

In some embodiments, the adapter unit comprises a monolithic, single-mode or multimode treatment laser diode and a beam homogenizer for homogenizing the laser light from the treatment laser diode, wherein the treatment laser diode and the beam homogenizer are configured to provide treatment laser light for a diagnostic instrument of an ophthalmic system without use of a fibre-optic cable for delivery of laser light to the adapter unit.

Generally, in some embodiments, the optical elements of the adapter unit comprise a beam homogenizer. In some embodiments, the beam homogenizer is a microlens array or a semi-random diffusing surface structure. For example, an "Engineered Diffuser" as available from Thorlabs Inc. or a microlens as available from Edmund Optics. The microlens is preferably made from precision fused silica substrates. In alternative embodiments, the beam homogenizer is a "Light Pipe Homogenizer" as available from Newport Corporation.

Generally, in some embodiments, the apparatus for ophthalmic treatment comprises an adapter-mounted (i.e. mounted as an adapter unit to a diagnostic instrument such as a slit lamp) monolithic, single mode or multimode treatment laser diode source and a lens configuration to collimate or focus light at a wavelength suitable for ophthalmic treatment from the treatment laser diode to a patient's eye. The advantage of this is that fewer components are needed and a compact design is facilitated. Preferably the system comprises a beam homogenizer. Preferably the system is free of external optical fibers or at least free of optical fibers feeding laser light from a remote treatment light source to an adapter unit.

In some embodiments, the apparatus for ophthalmic treatment further comprises a low-power (compared to the treatment direct diode laser) pilot light source, e.g. a pilot laser diode, for emitting a pilot light beam (e.g. having an average power of less than 5 mW, such as less than 1 mW) to serve as pilot (aiming) beam for the operator at a wavelength equal or dissimilar to the treatment wavelength. In some embodiments, the pilot light source is accommodated in the housing of the adapter unit.

In some embodiments, the adapter unit comprises a single treatment laser diode and, optionally, a pilot light source such as a pilot laser diode, thus providing a particularly compact and low-complex apparatus. In other embodiments, the adapter unit comprises two or more treatment laser diodes (and, optionally, a pilot light source such as a pilot laser diode), and the one or more optical elements are configured to combine/multiplex light from the two or more treatment laser diodes, e.g. using wavelength and/or polarization multiplexing. For example, to this end, the one or more optical elements may comprise a volume Bragg grating or a dichroic mirror. Accordingly, a particularly high-power treatment beam may be generated by a compact and versatile adapter unit. In some embodiments, the adapter unit even comprises three or mode treatment laser diodes that are multiplexed in order to obtain a higher power of the apparatus for ophthalmic treatment.

For example, in some embodiments, the adapter unit comprises:
a first monolithic, multimode treatment laser diode at a wavelength suitable for ophthalmic treatment configured to emit laser light with a substantially linear polarization state p1, and
a second monolithic, single mode or multimode treatment laser diode configured to emit laser light at a wavelength suitable for ophthalmic treatment and with a substantially linear polarization state p2 being orthogonal to p1, and
a polarization beam splitter configured to combine the emitted laser light from said first and second monolithic, single mode or multimode treatment laser diodes.

In some embodiments, the second treatment laser diode may be configured to emit laser light with a substantially linear polarization state p2 being orthogonal to p1 by mounting the second treatment laser diode at a 90 degree angle relative to the first, or by placing a half-wave plate after one of the diodes to rotate the polarization.

Preferably each of the laser diodes is configured to emit light at an average power of more than 100 mW, such as more than 200 mW, such as more than 300 mW, such as more than 400 mW, and less than 3000 mW, such as less than 2000 mW, such as less than 1500 mW, such as less than 1000 mW, such as less than 500 mW. In other embodiments, the treatment laser diode has an average power between 300-1000 mW. Preferably the apparatus is configured to allow the power of the combined light from the laser diodes to be adjusted and where the combined light may be adjusted to a maximum power of at least 1 W, preferably at least 1.5 W, more preferably more than 1.5 W, such as 2 W or more.

The ability to control various performance parameters of an adapter unit and, in particular, performance parameters associated with the treatment light beam is an important feature for most embodiments of an apparatus for ophthalmic treatment. These performance parameters may include one or more of the following: optical power, beam diameter, astigmatism, ellipticity, intensity noise, beam quality, wavelength, spectral line width, side-mode suppression ratio, beam focusing, beam pulse width, repeat interval of the pulses, beam pointing direction or a combination thereof. Depending on the application, some of these parameters should simply be stabilized whereas other parameters should be adjustable at the request of the user or as a part of an automated procedure.

To this end, the adapter unit may further comprise a control circuit, e.g. accommodated within said housing, thus providing an integrated device which, in some embodiments, may receive control commands from a user terminal remote from the adapter unit. The control commands from a remote user terminal may be communicated via a wired or a wireless connection. For example, the control commands may be indicative of commands to adjust one or more of the above performance parameters. The control circuit may e.g. be implemented as one or more control PCBs, which may include on-board firmware to provide commands to all sub systems on one or more of the following: laser source control, sub-system control, safety monitoring, and light pulse generation, temperature control.

The control circuit may be operable to adjust one or more controllable parameters of the adapter unit, e.g. at least in part responsive to control commands received from the user terminal. The control circuit may also be referred to as a laser controller. In particular, the controllable parameters of the adapter unit may e.g. include one or more injection currents of the treatment laser diode.

The control circuit may be operable to adjust the controllable parameters so as to adjust one or more performance parameters of the adapter unit, e.g. one or more of the performance parameters mentioned above, e.g. with respect of the treatment light beam output by the adapter unit. Some performance parameters may be adjustable directly while others may be adjusted by changing one or more other controllable parameters. The control circuit may be configured to adjust the performance parameters to respective predetermined or user-selected values and/or within predetermined or user-selected ranges and/or or to optimize one or more of the performance parameters.

For example, the control circuit may be configured to control a performance parameter of the emitted light by controlling an operating current of the treatment laser diode source.

In some embodiments, the treatment laser diode is mounted on one or more temperature control elements, e.g. one or more cooling elements such as a Peltier cooler, and the control circuit is configured to control the temperature of the treatment laser diode and/or of mechanical elements in a proximity of the treatment laser diode, e.g. by controlling an electrical current to the one or more temperature control elements. To this end, the adapter unit may comprise a temperature sensor operable to measure a temperature at, or in a proximity of, the treatment laser diode, and the control circuit may be configured to control an electrical current to the temperature control element.

The apparatus for ophthalmic treatment may further include one or more light detectors that monitor the laser output power. The signal from this/those detectors may be used to control the output power of the adapter unit. In particular, in some embodiments, the adapter unit comprises, preferably accommodated within the housing of the adapter unit, a light detector, e.g. a photo diode, operable to receive a portion of the emitted light from the treatment direct diode laser and to monitor an output power of the treatment direct diode laser.

The apparatus for ophthalmic treatment may further comprise a power supply, e.g. including an AC/DC converter, for providing electrical operating power to the adapter unit. When the power supply is provided as a separate unit external to the adapter unit and, in particular, in a housing separate from the housing of the adapter unit that accommodates the treatment direct diode laser, the adapter unit does not need to include any AC components such that the adapter unit only receives DC power. In some embodiments, the power supply comprises one or more batteries, e.g. rechargeable batteries. A battery-driven power supply may be integrated or directly attached to the housing of the adapter unit or it may be separate from the adapter unit and electrically connected to the adapter unit via a wired connection, e.g. a power cable. In some embodiments the adapter unit includes a receptacle to which a rechargeable battery may be removably connected so as to allow a user to selectively replace the battery.

The provision of an external user terminal and/or an external power supply allows the adapter unit to be designed as a thermally efficient platform. Nevertheless, the adapter unit may comprise active and/or passive cooling means, such as cooling ribs.

In some embodiments, the adapter unit comprises an input for receiving electrical power. In some embodiments, the only wired interface to the adapter unit is a wired connection for electrical operating power, preferably DC operating power. In alternative embodiments, the only wired interfaces to the adapter unit are a wired connection for electrical operating power and an additional interface for control signals to the adapter unit. In particular, no optical fibre connection for feeding light to the adapter unit is required.

The user terminal may include a foot switch configured to selectively activate emission of the treatment light beam to the subject's eye, e.g. by operating a shutter of the adapter unit or by turning on the operating current to the treatment direct diode laser. A foot switch may be a wired or a wireless device that may comprise redundant contacts for safety. The foot switch may be operable to be pressed by the user so as to cause the system to deliver the treatment light beam to the target tissue. The foot switch and the adapter unit may be communicatively connected to the user terminal.

The user terminal may comprise one or more of the following:
- a power input and AC/DC conversion circuitry, e.g. implemented as one or more PCBs; alternatively or additionally, the user terminal may comprise a battery.
- a user interface which may include knobs and a display and/or a touchscreen interface. The user interface allows the user to select the desired parameters, either by voice command or direct selection via e.g. knobs or a touchscreen interface. In some embodiments the user interface comprises a microphone or other voice recording device and a speech recognition component configured to recognize spoken commands. The user interface may further provide the user with information about the status of the system, e.g. by displaying such information or by means of audible, e.g. vocal feedback.

Wireless communication may be employed for communication between the user terminal and the control circuit. The wireless communication may use known standards, such as Bluetooth and other secure wireless methods of communication.

In some embodiments, the apparatus for ophthalmic treatment comprises a control unit to control operational parameters of the diagnostic instrument. The apparatus may further comprise an operating console for providing a user interface allowing a user to control operational parameters of the diagnostic instrument. It will be appreciated that the user terminal for controlling the adapter unit may be integrated into the operating console of the diagnostic instrument. Alternatively, the user terminal for controlling the adapter unit may be a separate device, different from the operating console of the diagnostic instrument. In particular, in some embodiments, an add-on ophthalmic treatment system may be provided that comprises the adapter unit, the user terminal and, optionally, a foot switch and/or a separate power supply and that can be operationally connected to an existing diagnostic instrument as described herein. It will be appreciated however, that the user terminal and the operating console may be communicatively coupled to each other, e.g. by a wired or wireless communications interface, e.g. so as to provide a user interface on both devices which may selectively be used by the operator or at least be operable as respective backup user interfaces.

The apparatus for ophthalmic treatment may further comprise a voice input and/or output unit configured to receive vocal input and/or to output audible outputs. The voice input and/or output unit may comprise a voice recognition system, e.g. embodied by a suitably configured signal processing unit and/or data processing unit. The voice recognition system receives vocal input from the operator and transforms the received vocal input to settings of the controllable parameters in a wired or wireless method of communication. In some embodiments the voice input and/or output system is comprised in the user terminal for controlling the adapter unit and is operable to receive voice commands and to transform the received voice commands into control commands to the adapter unit. In some embodiments, the voice input and/or output system is operable to process voice commands directed to both the diagnostic instrument and to the adapter unit.

Generally, vocal input may be in the form voice commands from an operator. Audible output may be indicative of parameters and status of the treatment direct diode laser or other suitable treatment light source. Accordingly, a person operating said apparatus for ophthalmic treatment is enabled to perform surgery with vocal control of controllable parameters of the adapter unit, thereby allowing the operator to control operation of the adapter unit and/or to monitor performance parameters of the treatment light source during surgery without having to remove the eyes from the eye piece of the diagnostic instrument and without moving visual focus from the site of the surgery, and without moving the hands away from the equipment or from a lens that the operator may hold to the eye of the patient. This allows the operator to more efficiently perform surgery and the performance of surgery is less tiring for the operator which in turn increases the efficiency and safety of the surgery.

The inventors have realised that adjustment of the power and/or the pulse width and/or repeat interval of the treatment beam are particularly useful parameters to control based on vocal input as these have to be adjusted frequently during the treatment.

Also, as the treatment is often performed as a sequence of a large number of light pulses, it has been realised that an audible feedback indicative of the number of pulses during a treatment (e.g. the number of already applied pulses or the remaining number of pulses still to be applied up to a target number of pulses) is particularly advantageous for an efficient and safe treatment.

It is a further advantage that treatment time is reduced and efficiency is improved, as the operator does not need to interrupt viewing through the diagnostic instrument for reading/confirming the parameters of the treatment light beam surgery because the parameters are controlled via vocal commands by the operator. A further advantage is that information about the output power and/or about other parameters is provided to the operator by audio feedback.

In some embodiments the user terminal comprises a suitable user interface allowing the control of the adapter unit without use of voice control, e.g. such that the user terminal allows the voice controlled option to be enabled/disabled from a suitable user-interface of the user terminal. In some embodiments, voice commands may be used in addition to non-vocal commands.

The voice control system may be responsive to a "wakeup" word or command that triggers the voice control system to respond to subsequent commands. In some embodiments, the voice control system is configured to provide an audible acknowledgement when receiving a voice command. For example, in response to the receipt of a voice command triggering a parameter change of a performance parameter of the adapter unit (e.g. the output power), the voice control system may audibly callout the parameter change.

In some embodiments, the user terminal includes the voice recognition system and the communications device. In some embodiments, the user terminal is embodied as a tablet computer or other portable or suitably compact processing device configured to be operable as a display and user interface. The tablet computer or other processing device may further comprise the communication interface for communicating control signals to the control circuit of the adapter unit, e.g. wirelessly such as via Wi-Fi, Bluetooth or another suitable communications technology. The tablet computer or other processing device may further comprise a speaker and/or microphone for providing the voice input and/or speech output.

The present disclosure relates to different aspects including the apparatus for ophthalmic treatment described above and in the following, corresponding apparatus, systems, methods, and/or products, each yielding one or more of the benefits and advantages described in connection with the first mentioned aspect, and each having one or more embodiments corresponding to the embodiments described in connection with the first mentioned aspect and/or disclosed in the appended claims.

In particular, according to one aspect, the present disclosure relates to an apparatus for ophthalmic treatment, such as photocoagulation or photo-thermal stimulation, wherein the apparatus comprises:
 at least one treatment light source configured to emit light;
 a control unit operable to control a power of the emitted light;
 a communication unit configured to receive vocal input and/or to output an audible output.

Generally, vocal input may be in the form of voice commands from an operator. Audible output may be indicative of parameters and status of the treatment light source. Accordingly, a person operating said apparatus is enabled to perform surgery with vocal control of parameters associated with the emitted light, thereby allowing the operator to control operation of the apparatus and/or to monitor performance parameters of the treatment light source during surgery without having to remove the eyes from the eye piece of a diagnostic instrument and without moving visual focus from the site of the surgery. This allows the operator to more efficiently perform surgery and the performance of surgery is less tiring for the operator, which in turn increases the efficiency and safety of the surgery.

According to yet another aspect, the present disclosure further relates to a medical laser system for ophthalmic treatment, such as photocoagulation or photo-thermal stimulation, the laser system comprising a slit-lamp or operating microscope apparatus and an adapter unit being in direct physical contact with said slit lamp or operating microscope apparatus, said adapter unit having an input and an output, the adapter unit being configured to receive electrical power at the input and emit laser radiation at the output, the adapter unit comprises
 a monolithic, single mode or multimode laser diode at a visible wavelength configured to emit radiation, and
 one or more lenses, beam shapers or beam homogenizers for adjusting a beam profile of the emitted radiation and to direct the emitted radiation to laser radiation at the output in a predetermined direction,
 wherein said predetermined direction coincides with a beam path of said slit-lamp or operating microscope apparatus to radiate a target area for ophthalmic treatment.

The present disclosure further relates to a medical laser system for ophthalmic treatment, such as photocoagulation or photo-thermal stimulation, the laser system comprising a slit-lamp or operating microscope apparatus and an adapter unit being in direct physical contact with said slit lamp or operating microscope apparatus, said adapter unit having an input and an output, the adapter unit being configured to receive electrical power at the input and emit laser radiation at the output, the slit-lamp adapter unit comprises
 a first monolithic, multimode laser diode at a visible wavelength configured to emit radiation with a substantially linear polarization state p1, and
 a second monolithic, single mode or multimode laser diode at a visible wavelength configured to emit radiation with a substantially linear polarization state p2 being orthogonal to p1, and
 a polarization beam splitter configured to combine emitted radiation from said first and second monolithic, single mode or multimode laser diodes, and
 one or more lenses, beam shapers or beam homogenizers for adjusting a beam profile of the emitted radiation and/or the combined emitted radiation and to direct the emitted radiation to laser radiation at the output in a predetermined direction,
 wherein said predetermined direction coincides with a beam path of said slit-lamp apparatus to radiate a target area for ophthalmic treatment.

The apparatus for ophthalmic treatment of the above-mentioned aspects and preferred embodiments are suitable for use by an operator for performing ophthalmic conditions of a patient, such as a diabetic or glaucoma disease. The apparatus enables the operator to perform surgery using therapeutic light, such as laser surgery, to the eye of a patient, where space is saved in the clinic by the compactness of the system.

The present disclosure further relates to an adapter unit for use with an apparatus for photothermal ophthalmic treatment as disclosed herein. In particular, the present disclosure relates to an adapter unit mountable to a diagnostic instrument, the diagnostic instrument being configured to emit illumination light from an illumination output along a free-air illumination output path towards a target area for ophthalmic treatment and to receive light from the target area along a free-air viewing path and to provide a magnified view of the target area; wherein the adapter unit comprises:

a housing detachably mountable to the diagnostic instrument;

at least one treatment direct diode laser source positioned within the housing, the direct diode laser comprising a treatment laser diode configured to emit light at a wavelength suitable for ophthalmic treatment in the wavelength range of 480 and 632 nm, one or more optical elements configured to direct the emitted light as a treatment light beam along at least a portion of said free-air illumination output path and/or free-air viewing path when the housing is mounted to said diagnostic instrument; and wherein at least one of the optical elements is configured to extend into at least one of the free-air viewing path and the free-air illumination output path of the diagnostic instrument when the housing is mounted to said diagnostic instrument in an operational position.

In some embodiments, the housing is mountable to the diagnostic instrument with the treatment direct diode laser being positioned above or in line with the viewing path.

Generally, some embodiments of the adapter unit—i.e. a slit lamp adapter or, alternatively, an adapter for an operating microscope—direct the treatment light beam into a subject's eye. The adapter unit comprises a treatment direct diode laser and optical elements arranged to form an optical train that is operable to focus the light as a treatment light beam to a user-selectable spot sizes at a target tissue. The adapter unit may comprise a mirror element, such as a dichroic mirror operable to reflect the treatment light beam and, optionally, an aiming/pilot beam towards the target but to allow other visible wavelengths to pass. The adapter unit may further comprise one or more eye-safety filters operable to protect a user from light flashback through the visual axis. The adapter unit may further comprise a mechanical mounting element operable to adapt to pre-existing diagnostic slit lamps and operating microscopes. The adapter unit may further comprise a control circuit, e.g. a PCB, operable to control operation of the treatment direct diode laser and to communicate with a user terminal, e.g. for facilitating spot size selection.

Embodiments of the adapter unit may be embodied as a single unit comprising a single housing accommodating at least the treatment direct diode laser, a control circuit and the one or more optical elements. The optical elements of the adapter unit may be positioned within said housing and/or attached to said housing. In particular, the single housing may accommodate (either within or otherwise attached thereto) all optical elements required for directing light from the treatment direct diode laser accommodated within the housing in free space towards a subject's eye along the illumination output path of the diagnostic instrument. The housing further comprises, or has attached thereto, a mounting element for mounting the adapter unit to the diagnostic instrument.

DETAILED DESCRIPTION

Various aspects and embodiments of an apparatus for ophthalmic treatment disclosed herein will now be described with reference to the drawings.

Figure 1A:
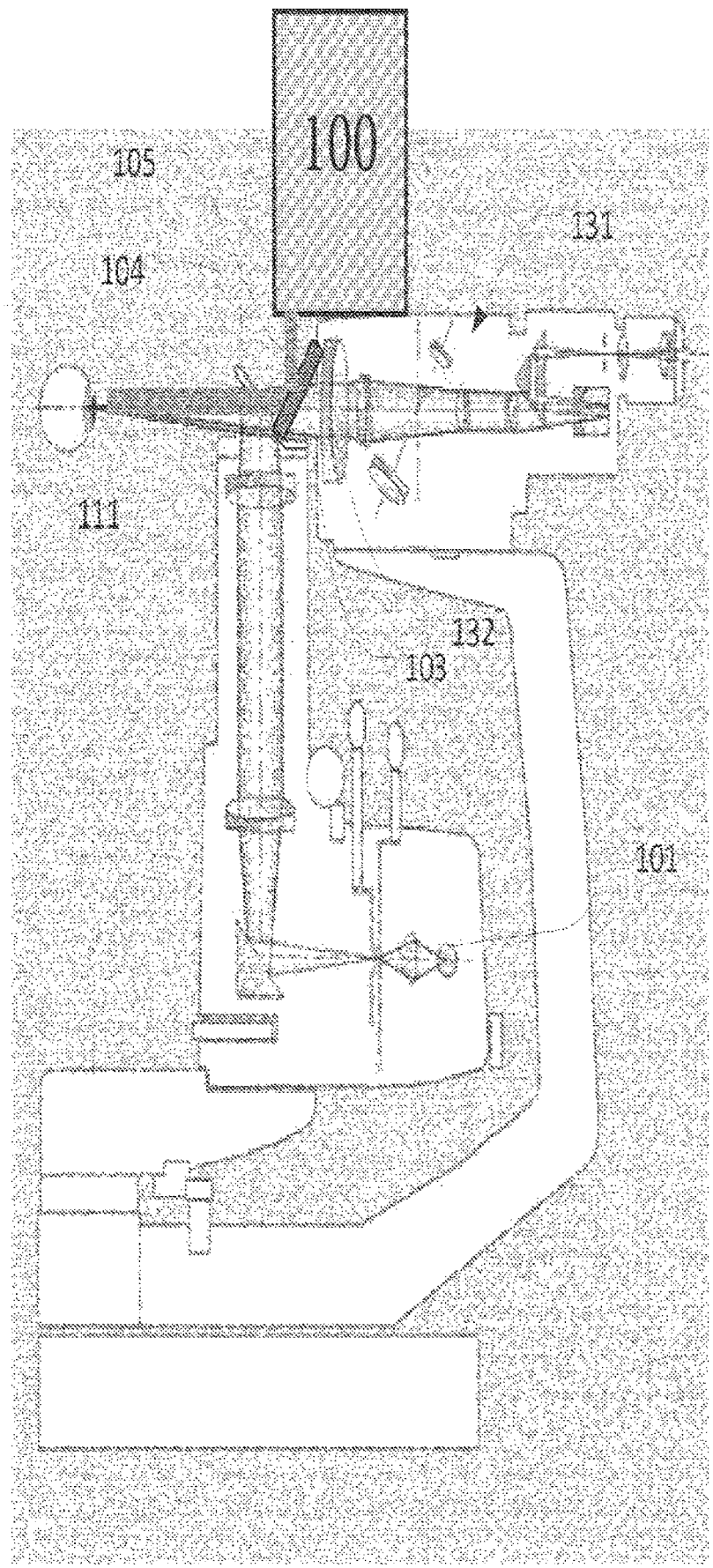
FIGS. 1A-C show schematic illustrations of examples of an apparatus for ophthalmic treatment.

FIG. 1A schematically shows an apparatus for ophthalmic treatment according to a preferred embodiment of the present invention. The figure schematically shows an adapter unit 100 that comprises a monolithic, single mode or multimode treatment laser diode and that is attached to the slit lamp via a tonometer mount. The slit lamp includes a magnifying optical device 131, such as a microscope or zoom telescope, configured to receive light at a viewing input 132 along a viewing path 103 from a target area. The central part of the slit lamp includes a white light source 101 that is used to illuminate a target area in the eye 102 of the patient. This white light is directed, by means of a mirror 104, onto an illumination output path 111 that coincides with the optical viewing path 103 of the operator at the designed focal point of the diagnostic instrument at the target area. In the same fashion, the light 105 from the laser is directed towards the target area along a treatment beam path such that it coincides with the viewing path, at least at the target area.

Figure 1B:
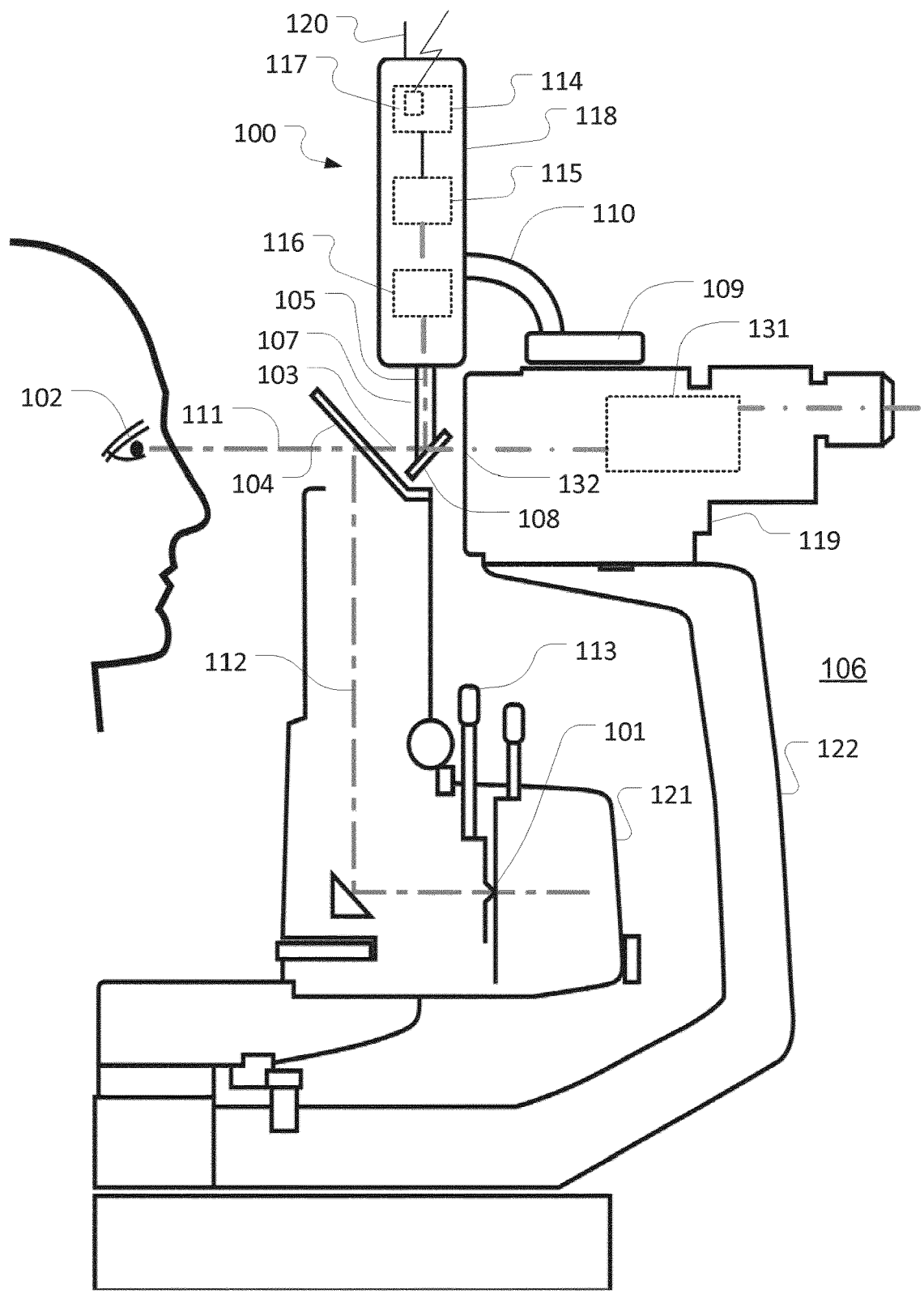

FIG. 1B schematically shows an apparatus for ophthalmic treatment according to a preferred embodiment of the present invention. The apparatus for ophthalmic treatment of FIG. 1B is similar to the embodiment of FIG. 1A in that it comprises a slit lamp apparatus 106 having attached thereto an embodiment of an adapter unit 100 as described herein. The slit lamp apparatus comprises a magnifying optical device 131, such as a microscope or zoom telescope, accommodated in a viewer housing 119 of the slit lamp. The magnifying optical device allows an operator to view a magnified image of parts of the subject's eye 102 along a viewing path 103. The viewing path extends between the subject's eye 102 and a viewing input 132 of the magnifying optical device. The bottom part of the slit lamp comprises a white light source 101 that is used to illuminate the eye 102 of the patient. The slit lamp comprises a mirror 104 operable to direct the white light 112 from the light source onto an illumination output path 111 that coincides, at least at the target area, with the viewing path 103 of the operator. The illumination path thus exits the slit lamp at the mirror 104, which in this example defines the output of the slit lamp for the illumination light, and extends to the subject's eye 102.

The adapter unit 100 comprises a housing 118 from which a mounting arm 110 or other mounting element is attached. The viewer housing 119 of the slit lamp is provided with a tonometer mount 109 or other suitable mounting platform to which the mounting arm 110 can be detachably connected. In this embodiment, the tonometer mount 109 is positioned above the viewing path 103 and, more particularly, above the viewer housing 119.

The adapter unit 100 comprises a monolithic, single mode or multimode treatment laser diode 115 and a laser controller 114 for controlling the treatment laser diode. The adapter unit further comprises one or more optical elements 116 such as one or more lenses, one or more beam homogenizers, etc. The laser controller, the treatment laser diode and the optical elements are all accommodated within housing 118. The adapter unit further comprises a mirror 108, e.g. a dichroic mirror, mounted on an arm 107 extending downwards from the housing 118. The adapter unit is mounted to the tonometer mount 109 such that the mirror 108 extends towards or even into the viewing path 103. The optical elements 116 direct the laser beam 105 onto the mirror such that the mirror directs the treatment laser beam towards the subject's eye. Hence the laser beam 105, the illumination output path and the viewing path 103 are all directed to coincide at the target tissue in the subject's eye 102.

The adapter unit 100 is located above the illumination output path and above the viewing path such that the arm 107 with the mirror 108 extends downwards with the mirror extending towards or even into the viewing path 103 and such that the laser beam 105 extends downwards from the treatment laser diode towards the mirror 108, i.e. the treatment laser diode 115 and, in this example, the entire housing 118 accommodating the treatment laser diode, are positioned above the viewing path 103.

Accordingly, the adapter unit 100, when mounted to the tonometer mount 109, does not interfere with the structural components of the slit lamp 106, such as the lamp housing 121 accommodating the white light source, the stand 122 supporting the magnifying optical device or with the control elements 113 that allow the operator to operate the slit lamp, or with any parts of the subject's body.

Moreover, the adapter unit 100 is an integrated unit that comprises the treatment laser diode, laser controller, the optical elements 116 inside housing 118 and the mirror 108 for generating the treatment laser beam 105.

In the embodiment of FIG. 1B, the laser controller 114 comprises a wireless communications circuit 117 allowing the laser controller to receive control commands from a user terminal and to transmit values of operational parameters such as performance parameters to the user terminal. Accordingly, in this embodiment, the only wired interface to the adapter unit is a power cable 120 for feeding electrical power to the laser controller and treatment laser diode. Preferably, the power cable feeds a low-voltage DC current to the adapter unit. To this end the power cable 120 may be connected to a suitable external power supply which may comprise a suitable AC/DC converter. In alternative embodiments, the communication to/from the laser controller may be a wired communications interface rather than a wireless interface. In such an embodiment, the adapter unit comprises an additional wired control connection. In alternative embodiments, the adapter unit may be powered by a battery, e.g. a battery accommodated within the housing 118, or attached thereto, or by a remote, battery-driven power supply unit via a power cable.

The mounting arm 110 may be rotatably coupled to the tonometer mount 109 such that the adapter unit may be swivelled between an operational position (as shown in FIG. 1B) with the mirror 108 extending towards or even into the viewing path 103 and a parking position where the mirror does not direct the laser beam towards the subject's eye. This may be useful in some embodiments, as the operator may thus have an unobstructed view towards the subject over the housing of the slit lamp.

Embodiments of slit lamps as illustrated in FIGS. 1A-B where the illumination light 112 is fed into the illumination output path from below, are also referred to as "Zeiss-type" slit lamps. In the following, and embodiment based on a so-called "Haag-Streit-type" slit lamp, where the illumination light is fed into a combined illumination output path from above, will be described with reference to FIG. 1C.

Figure 1C:
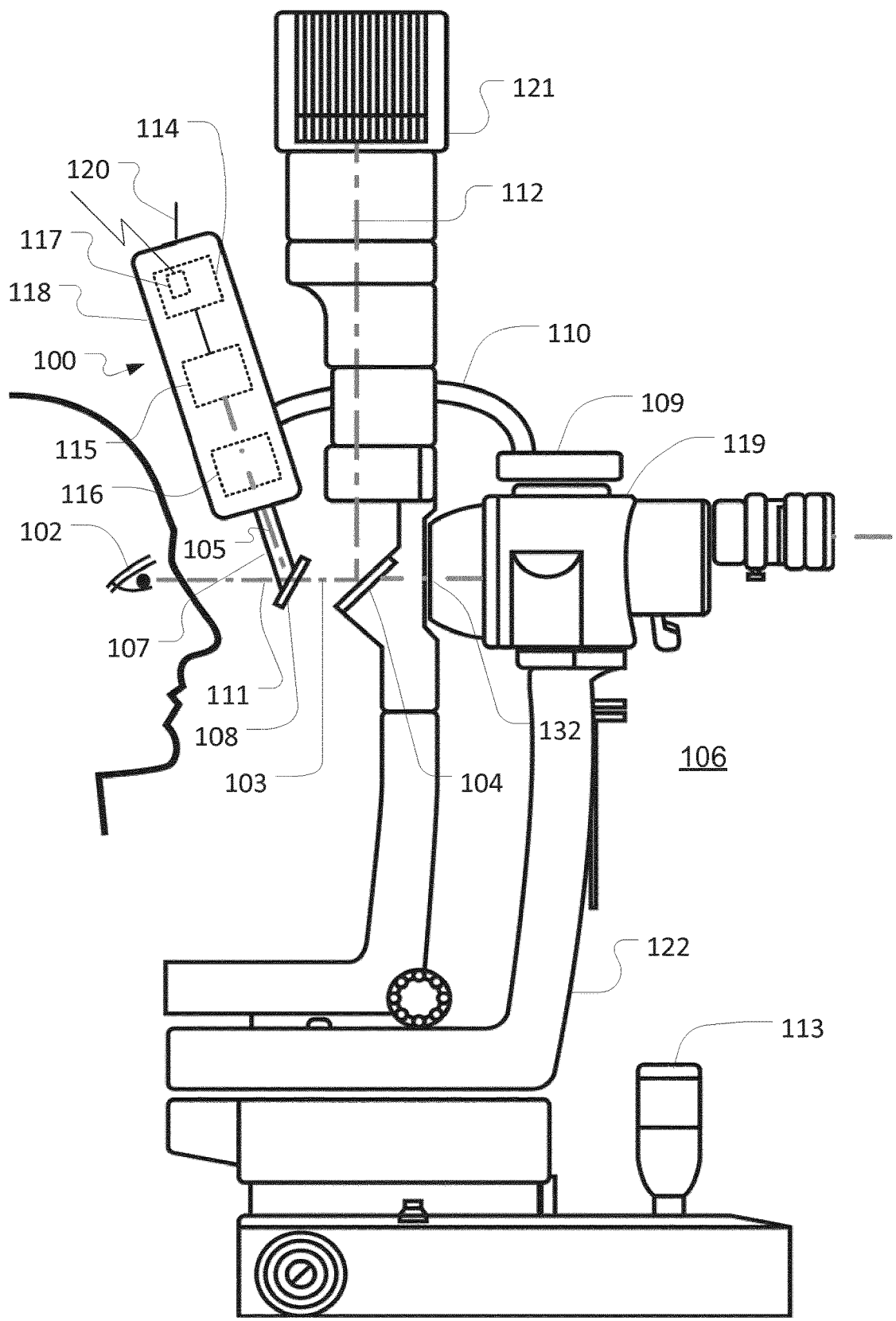

FIG. 1C shows schematically an apparatus for ophthalmic treatment according to a preferred embodiment of the present invention. The apparatus for ophthalmic treatment of FIG. 1C is similar to the embodiments of FIGS. 1A-B in that it comprises a slit lamp apparatus 106 having attached thereto an embodiment of an adapter unit 100 as described herein. The slit lamp apparatus comprises a magnifying optical device (not explicitly shown), e.g. a microscope or zoom telescope, accommodated in a viewer housing 119. The magnifying optical device allows an operator to view a magnified image of parts of the subject's eye 102 along a viewing path 103 extending between the eye and a viewing input 132 of the magnifying optical device. The slit lamp further comprises a white light source that is used to illuminate the eye 102 of the patient. The slit lamp comprises a mirror 104 operable to direct the white light 112 from the light source onto an illumination output path 111 that, at least at the target area, coincides with the viewing path 103 of the operator. The illumination path thus exits the slit lamp at the mirror 104, which in this example defines the output of the slit lamp for the illumination light, and extends to the subject's eye 102.

In contrast to the embodiments of FIGS. 1A-B, the white light source of this embodiment is positioned in a lamp housing 121 that is positioned above the illumination output path 111, i.e. the illumination light 112 is directed downwards from the light source to the mirror 104.

As in the embodiments of FIGS. 1A-B, the adapter unit 100 comprises a housing 118 from which a mounting arm 110 or other mounting element is attached. The viewer housing 119 of the slit lamp is provided with a tonometer mount 109 or other suitable mounting platform to which the mounting arm 110 can be detachably connected. In this embodiment, the tonometer mount 109 is positioned above the viewing path 103 and, in particular, above the viewer housing 119.

The adapter unit 100 comprises a monolithic, single mode or multimode treatment laser diode 115 and a laser controller 114 for controlling the treatment laser diode. Generally, in this and other embodiments, the treatment laser diode may e.g. be any suitable laser diode emitting laser light at an intensity and wavelength suitable for therapeutic treatment of a subject's eye. The treatment laser diode may be a direct diode laser. An example of a suitable laser diode is disclosed in "1 W AlInGaN Based Green Laser Diodes," by S. Masui, T. Miyoshi, T. Yanamoto, and S. Nagahama, 2013 Conference on Lasers and Electro-Optics Pacific Rim, (Optical Society of America, 2013), paper WH3_1. Another example is disclosed in "Recent Improvement in Nitride Lasers", by Shingo Masui et al.; Gallium Nitride Materials and Devices XII, edited by Jen-Inn Chyi et al., Proc. of SPIE Vol. 10104.

The adapter unit further comprises one or more optical elements 116 such as one or more lenses, one or more beam homogenizers, etc. The laser controller, the treatment laser diode and the optical elements 116 are all accommodated within housing 118. The adapter unit further comprises a mirror 108 mounted on an arm 107 extending downwards from the housing 118. The adapter unit is mounted to the tonometer mount 109 such that the mirror 108 extends towards the viewing path 103. The optical elements 116 direct the laser beam 105 onto the mirror such that the laser beam is directed towards the subject's eye, all as described in connection with FIG. 1B.

The adapter unit 100 is located above the illumination output path and above the viewing path such that the arm 107 with the mirror 108 extends downwards with the mirror extending towards or even into the viewing path 103 and such that the laser beam 105 extends downwards from the treatment laser diode towards the mirror 108, i.e. the treatment laser diode 115 and, in this example, the entire housing 118 accommodating the treatment laser diode, are positioned above the viewing path 103.

As is illustrated in FIG. 1C, also in this embodiment, the adapter unit 100, when mounted to the tonometer mount, does not interfere with the structural components of the slit lamp adapter, such as the housing 121 accommodating the white light source, the stand 122 supporting the magnifying optical device or with the control elements 113 that allow the operator to operate the slit lamp or with any parts of the subject's body. Moreover, the adapter unit 100 is an integrated unit that comprises the treatment laser diode, laser controller, the optical elements 116 inside housing 118 and the mirror 108 for generating the treatment laser beam 105.

The laser controller 114 comprises a wireless communications circuit 117 and power to the adapter unit is provided via cable 102, all as described in connection with FIG. 1B. Also as in FIG. 1B, the mounting arm 110 may be rotatably coupled to the tonometer mount 109 such that the adapter unit may be swivelled between an operational position and a parking position.

Figure 2:
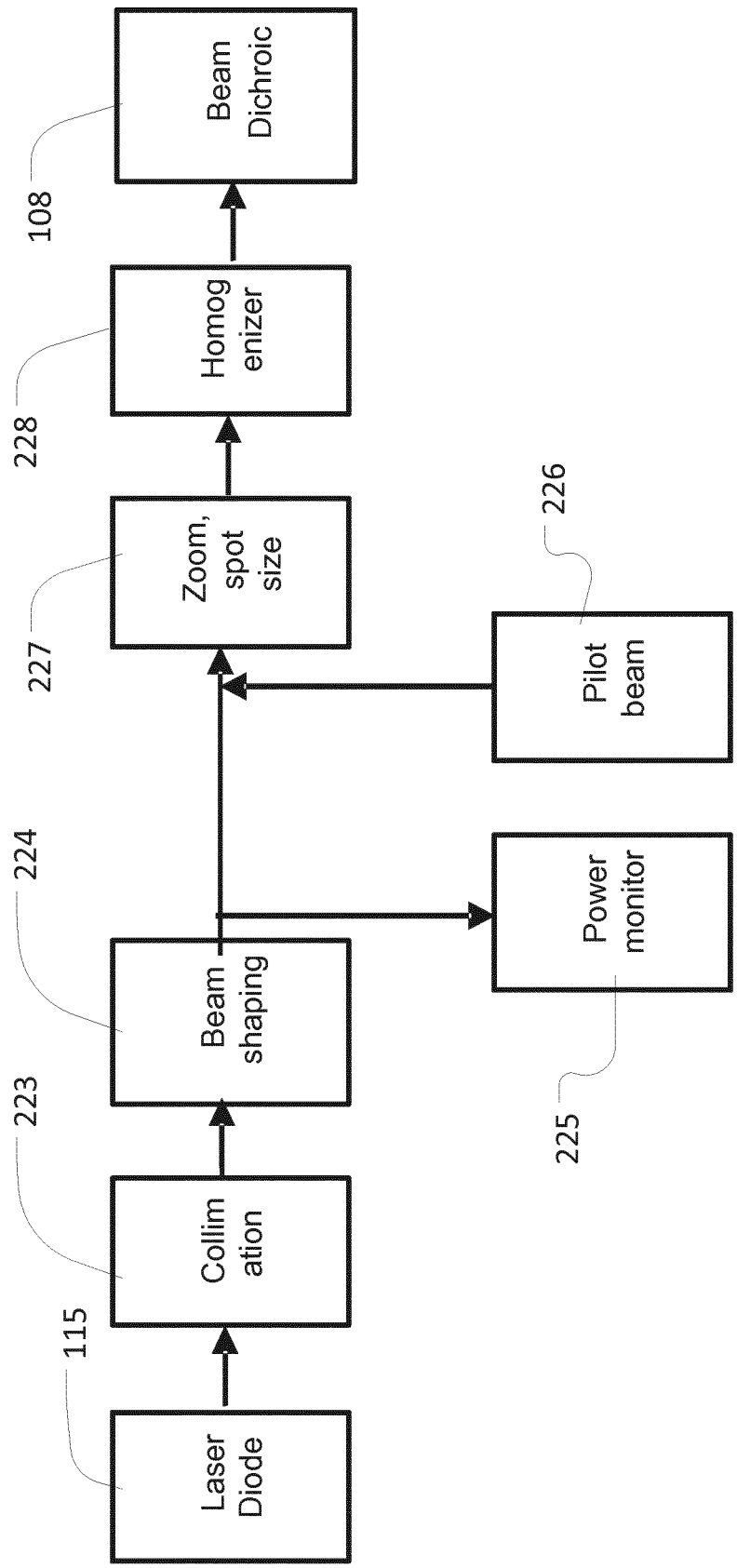
FIG. 2 shows a block diagram of elements of an optical design for an adapter unit for an apparatus for ophthalmic treatment.

FIG. 2 is a schematic block diagram that shows an optical path from a treatment laser diode towards the eye of a patient. The diverging light from the treatment laser diode 115 is collimated by a collimator 223 and directed to a beam shaping unit 224, which takes an elliptical beam of the treatment laser diode and re-shapes this beam to become circular. A small portion of the beam is directed, e.g. by means of a beam splitter, towards a power monitoring unit 225, e.g. a photo diode or other type of light detector. The monitored power may be fed to the laser controller which may then ensure stable laser operation. The device may further include a mechanical shutter (not explicitly shown). This may be used for controlling the emission of the treatment laser diode (or of the adapter unit), and also provide additional safety. A pilot beam source 226 (e.g. a low-power pilot laser diode) outputs a pilot beam which may be added to the beam path so that the operator can easily aim the laser beam. A zoom unit 227 controls the spot size. It comprises a telescope, which can vary the beam diameter. A homogenizer 228 ensures that the light intensity is distributed uniformly across the focused spot in the eye of the patient. Finally, a beam dichroic 108 enables the laser light to be positioned within the optical path of the slit lamp. All of the above components may be accommodated within, or at least attached to, a single housing, e.g. the housing 118 of the embodiments of FIGS. 1B-C. For example, in some embodiments all the above components except the dichroic are accommodated in a single housing and the beam dichroic is attached to the housing via a suitable arm. It will be appreciated that, in some embodiments, not all of the above elements will be present and/or additional elements will be present.

Figure 3:
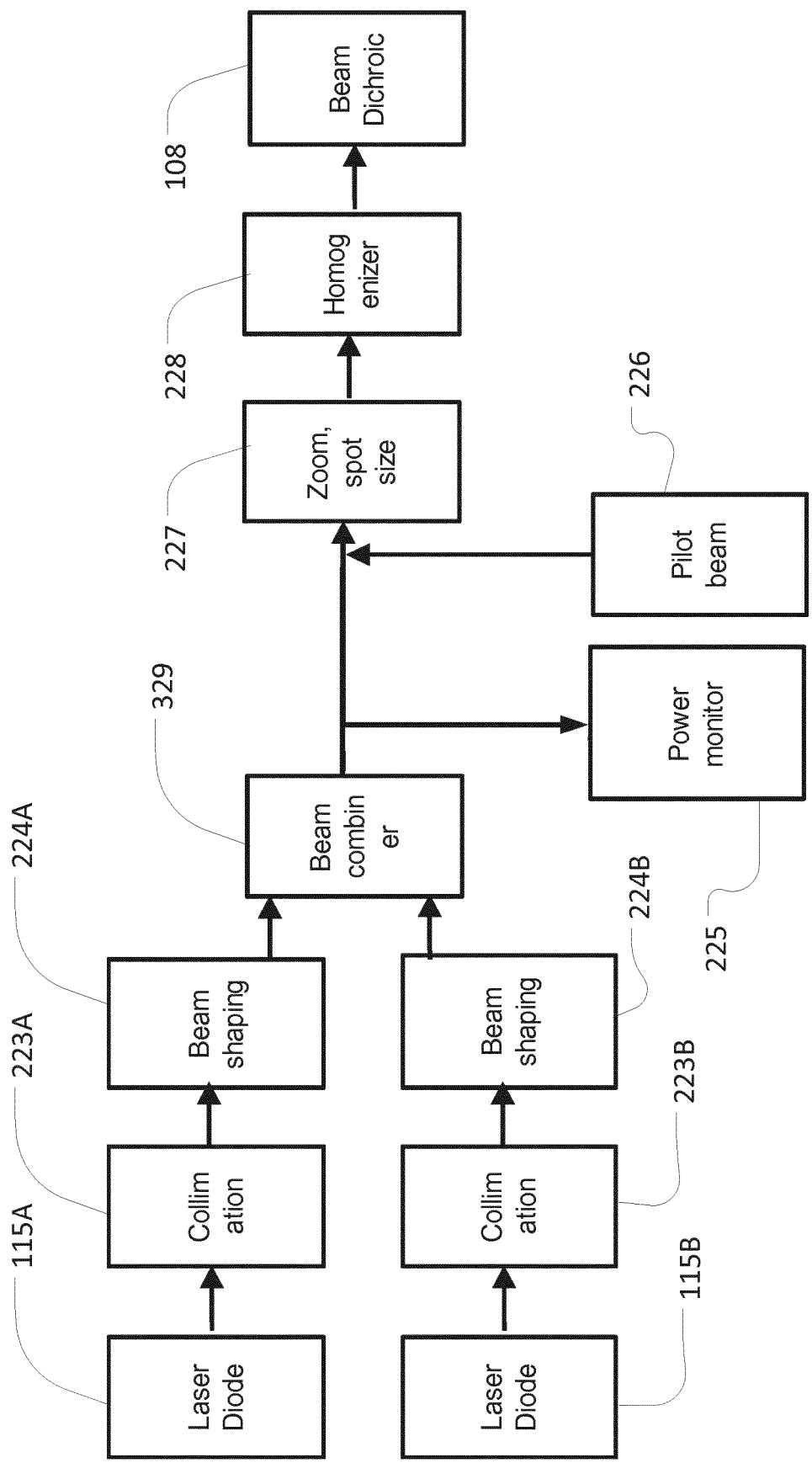
FIG. 3 shows another block diagram of elements of an optical design for an adapter unit for an apparatus for ophthalmic treatment, wherein two treatment laser diodes are used.

FIG. 3 shows a diagram illustrating an optical path of an adapter unit. The optical path shown in FIG. 3 includes similar elements as the optical path of FIG. 2. FIG. 3 shows a preferred embodiment where a first and a second treatment laser diode, 115A and 115B, respectively, are used in the system. The outputs of the respective treatment laser diodes are collimated by collimators 223A and 223B, respectively and shaped by beam shaping units 224A and 224B, respectively. The collimated and circular laser beams are then addition combined in a beam combiner 329. The remainder of the optical path is as described in connection with FIG. 2. A preferred method is to rotate the second diode 90 degrees around the axis defined by the emitted laser beam. With such rotation, the polarisation of this second laser beam is perpendicular to the first laser beam. In such an embodiment, a polarisation beam splitter (PBS) is well suited as a beam combiner.

Figure 4:
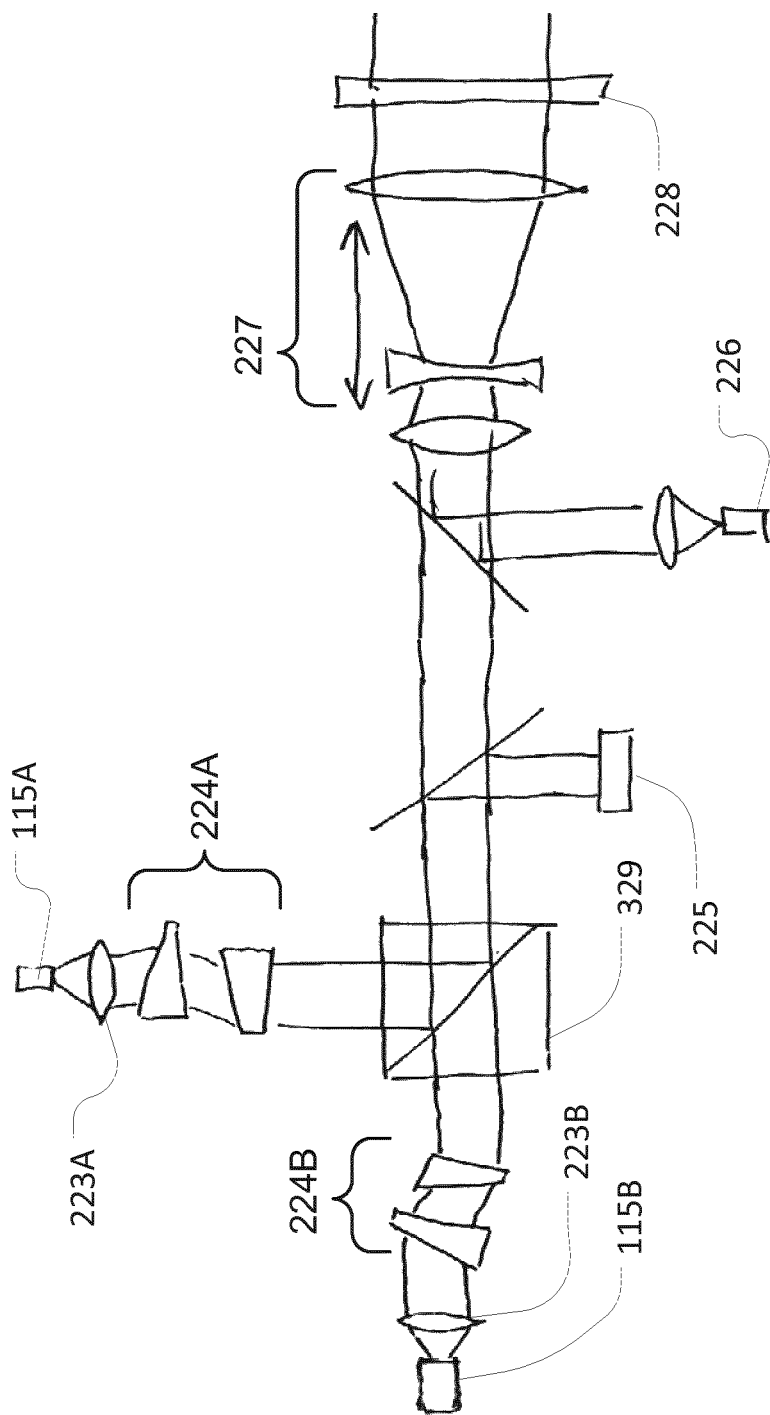
FIG. 4 shows a schematic illustration of elements of an optical design for an adapter unit for an apparatus for ophthalmic treatment, wherein two treatment laser diodes are used.

FIG. 4 shows a schematic illustration of elements of an optical design for an adapter unit for an apparatus for ophthalmic treatment, wherein two treatment laser diodes 115A and 115B, respectively, are used. The figure shows emitted light from two treatment laser diodes 115A-B being combined with a Polarization Beam Splitter (PBS) 329. Preferably the two treatment laser diodes are substantially linear polarized and are positioned/oriented in such a manner that their polarizations are orthogonal to each other. Preferably, the positioning/orientation is by way of rotating one diode relative to the other. This positioning/orientation in combination with the PBS element enable a beam combination with efficiency of 90% or more. Preferably, the system also comprises a zoom/spot size adaptor 227 and a homogenizer 228 to provide for example a substantially uniform spot size (for example a so-called top-hat profile). Moreover, preferably, the system comprises collimators 223A-B and beam shaping units 224A-B in the beam paths of the respective treatment laser diodes 115A-B and a pilot beam source 226 (e.g. a low-power pilot laser diode) and power monitor 225 as described above. Preferably, the laser diodes are electronically shuttered; alternatively, the system may comprise a shutter, e.g. positioned between the power monitor 225 and the pilot beam source 226. As in the previous embodiments, the emitted laser light may be directed towards the target area by a suitable mirror (not explicitly shown in FIG. 4).

Generally, in the above embodiments, as well as in other embodiments, the optical elements may comprise one or more elements for beam shaping and/or homogenization, e.g. as separate elements or as a combined unit. In some embodiments, the beam shaper unit and/or the homogenizer comprises a diffuser or microlens array. The diffuser or microlens array may be operable to provide a top-hat beam profile. Alternative or additional elements that may also be used as optical elements in embodiments of the adapter unit disclosed herein include:

One or more axicons and/or Powel lenses for top hat beam shaping, e.g. as described in Ola Willstrand: "Intensity distribution conversion from Gaussian to Top-Hat in a single-mode fiber connector", Master's Thesis, Lund University, Sweden, 25 Jan. 2013 An axicon is a conical prism defined by its alpha (a) and apex angles. Unlike a converging lens (e.g. a plano-convex (PCX), double-convex (DCX), or aspheric lens), which is designed to focus a light source along the optical axis, the design of an axicon focuses a light source to a line consisting of multiple points along the optical axis.

A spatial light modulator, i.e. an optical element that imposes some form of spatially varying modulation on a beam of light, e.g. operable for custom beam shaping and display of laser settings inside an eye.

One or more deformable mirrors, i.e. mirrors whose surface can be deformed, e.g. operable for custom beam shaping.

One or more digital light processing devices, i.e. a device based on optical micro-electro-mechanical technology that uses a digital micromirror device, e.g. operable for on/off switching of certain parts of the beam, enabling a custom beam profile on the eye.

One or more apertures, e.g. operable in combination with reimaging of an aperture plane onto the eye.

An anamorphic prism pair.

Alternatively or additionally, some embodiments of the adapter unit disclosed herein may be operable to perform beam shaping to so-called doughnut shaped beam profiles. Methods and devices for this include axicons and vortex retarders (e.g. Zero-Order Vortex Half-Wave Retarders as available from Thorlabs Inc.). Vortex retarders may allow an implementation involving lower costs.

Figure 5:
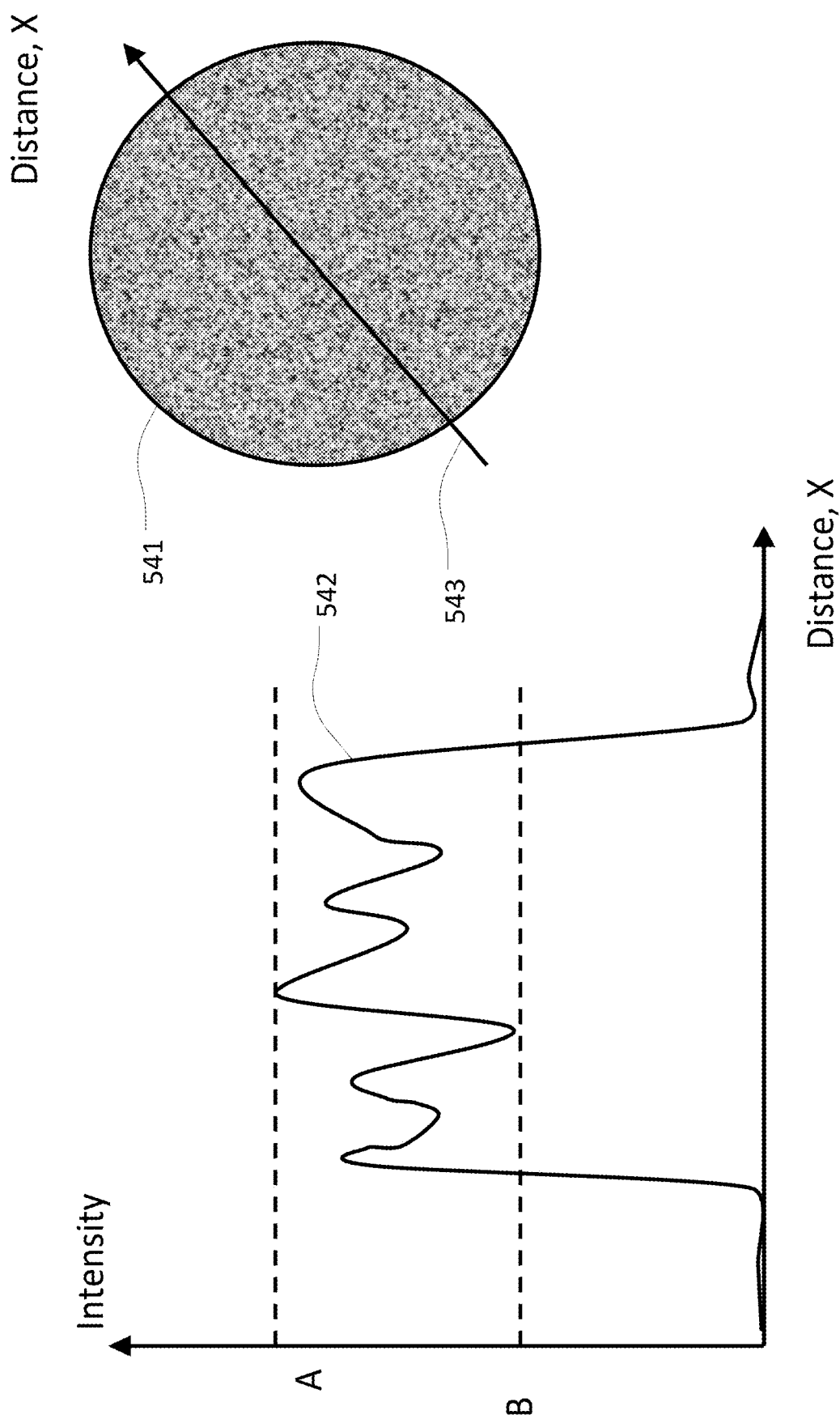
FIG. 5 shows a schematically how to measure homogeneity of beam.

FIG. 5 shows how homogeneity may be defined. A beam focus 541 similar to the focus in the patient's eye is made, and the intensity profile 542 is measured using a laser beam profiler. A profile analysis can now be made, where the intensity variation across the spot 541 is measured along a direction as indicated by arrow 543. The homogeneity H can be defined as $H=(1-2(A-B)/(A+B))*100\%$, where A is the maximum of the intensity profile and B is the minimum of the intensity profile. Preferably, the homogenizer is adapted to provide a homogeneity with H greater than 50%, such as greater than 75%, such as greater than 90%. Alternatively, the homogeneity may be defined as a Root Mean Square (RMS) of the intensity profile.

Figure 6:
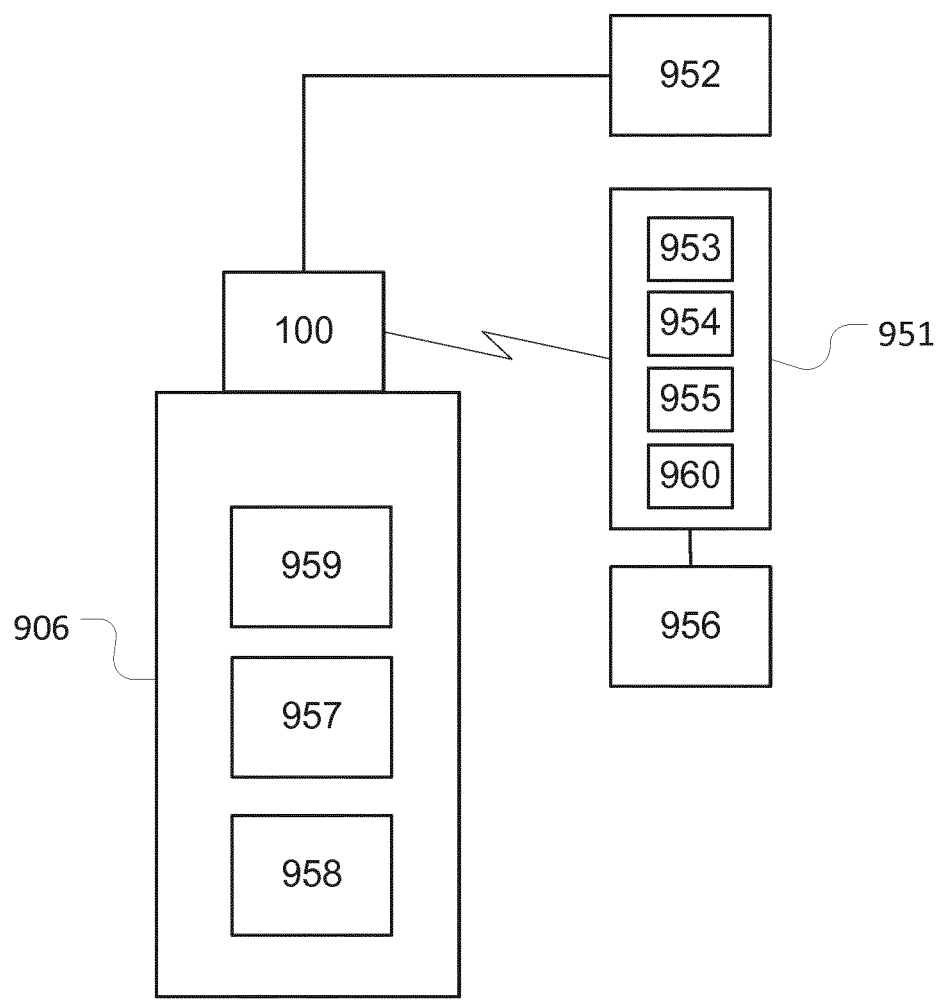
FIG. 6 shows a schematic block diagram of an apparatus for ophthalmic treatment.

FIG. 6 shows a schematic block diagram of an apparatus for ophthalmic treatment as disclosed herein.

The apparatus for ophthalmic treatment comprises a diagnostic instrument 906 and an adapter unit 100 mounted to the diagnostic instrument as described herein, e.g. as described in any of FIGS. 1A-C.

The system further comprises a user terminal 951 in wireless communication with the adapter unit 100, and a power supply unit 952 electrically coupled to the adapter unit 100. The power supply unit provides DC operating power to the adapter unit and the user terminal provides a user interface to the operator and communicates control commands to the adapter unit. The power supply unit may be battery-powered or configured to receive external power, e.g. AC power. The power supply unit 952 may also be intergareted into or directly attached to the housing of the adapter unit 100; for example, the adapter unit 100 may comprise a replaceable, e.g. rechargeable, battery. The user terminal may further receive values of operational parameters such as performance parameters from the adapter unit. The power supply unit and the user terminal may be embodied as separate units or as a single control unit. As described herein, the user terminal may provide a voice interface allowing for a hands-free control of performance parameters of the adapter unit. To this end, the user terminal may include a microphone 953, and loudspeaker 954 and a processing unit 955 implementing a voice recognition system. Preferably, the voice recognition system is a self-contained system that operates without the need to communicate with a remote host. However, in alternative embodiments, the voice recognition system may be a distributed system where at least a part of the voice recognition process is performed by a remote host system. Alternatively or additionally, the user terminal may comprise one or more other user interface devices 960, such as knobs, switches, a display, a touch screen and/or the like. The user terminal may further comprise, or be coupled to, a foot switch 956.

The diagnostic instrument comprises a power supply 959, a control unit 957 and an operating console 958, e.g. embodied as separate units or as a single, integrated unit. The user terminal 951 for controlling the adapter unit may be integrated into or separate from the operating console of the diagnostic instrument. Similarly, the power supply unit 952 and the power supply unit 959 may be embodied as separate units or as a single, integrated power supply.

The above detailed description refers to specific embodiments of the various aspects disclosed herein including various elements and features. In particular, embodiments of a medical laser system for ophthalmic treatment, such as photocoagulation or photo-thermal stimulation have been described. The described embodiments comprise an embodiment of a monolithic casing mounted above or in line with the viewing axis that encompasses laser(s), control electronics and beam manipulating and steering optics controlled by and external wireless user interface and emitting therapeutic laser light at a wavelength suitable for ophthalmic treatment, such as in the visible and/or near-infrared spectrum.

Also, embodiments a medical laser system for ophthalmic surgery, such as photocoagulation or photo-thermal stimulation, have been described that comprise a slit-lamp or operating microscope apparatus and an adapter unit being in direct physical contact with said slit lamp or operating microscope apparatus, said adapter unit having an input and an output, the adapter unit being configured to receive electrical power at the input and emit laser radiation at the output, the adapter unit comprises a monolithic, single mode or multimode laser diode at a visible wavelength configured to emit radiation, and one or more lenses, beam shapers or beam homogenizers for adjusting a beam profile of the emitted radiation and to direct the emitted radiation to laser radiation at the output in a predetermined direction, wherein said predetermined direction coincides with a beam path of said slit-lamp or operating microscope apparatus to radiate a target area for ophthalmic surgery.

Furthermore, embodiments of a medical laser system for ophthalmic surgery, such as photocoagulation or photo-thermal stimulation, have been described that comprise a laser device configured to emit radiation at a visible wavelength; wherein the laser device comprises a laser source configured to emit a source radiation, the laser source comprising:

monolithic, single mode or multimode laser diode;

beam shaping optics configured to homogenize said source radiation;

a control unit to control the power of the source radiation;

a communication unit configured to receive verbal input (such as oral or speech input from an operator) and output audible signals (such as reading out loud the power of the radiation source) and wireless communication between the user interface and the control electronics, whereby a person operating said medical device is enables to perform surgery with vocal control of laser parameters.

It will be appreciated that other embodiments may include alternative or additional elements or features. For example, in the above embodiments, the treatment light source comprises a laser diode. It will be appreciated that other embodiments may be embodied with other types of treatment light sources.

In the claims enumerating several means, several of these means can be embodied by one and the same element, component or item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, elements, steps or components but does not preclude the presence or addition of one or more other features, elements, steps, components or groups thereof.

The invention claimed is:

1. An apparatus for photothermal ophthalmic treatment, in particular photocoagulation or photo-thermal stimulation, the apparatus comprising a diagnostic instrument and an adapter unit, the diagnostic instrument being configured to emit illumination light from an illumination output along a free-air illumination output path towards a target area, to receive light from the target area along a free-air viewing path and to provide a magnified view of the target area, wherein the adapter unit comprises:
   a housing detachably mountable to said diagnostic instrument, said diagnostic instrument including a slit lamp;
   at least one treatment direct diode laser source positioned within the housing; the direct diode laser source comprising a treatment laser diode positioned within the housing and configured to emit light suitable for photothermal ophthalmic treatment at a wavelength suitable for the photothermal ophthalmic treatment in the wavelength range of 510 and 580 nanometers (nm) and with an average power of greater than 100 milliWatts;
   a pilot light source for emitting a pilot light beam of less than 5 milliWatts;
   one or more cooling elements coupled to the direct diode laser source;
   a laser controller configured to control at least the treatment laser diode;
   one or more optical elements configured to direct the emitted light from the treatment direct diode laser source as a treatment light beam towards the target area and to direct the pilot light beam towards the target area when the housing is mounted to said diagnostic instrument; and wherein the treatment laser diode and pilot light beam are located above said viewing path responsive to the housing being mounted to said diagnostic instrument and wherein at least one of the optical elements is a dichroic mirror that is mounted to an arm that extends downward into the free-air viewing path of the diagnostic instrument responsive to the housing being mounted to said diagnostic instrument in an operational position, the dichroic mirror reflecting the treatment laser beam and pilot light beam towards the target area.

2. The apparatus according to claim 1, wherein one or more of the optical elements are configured to shape the treatment beam such that it has a spot size in a free space focal plane of between 50 micrometers (μm) and 500 μm diameter.

3. The apparatus according to claim 1, wherein the treatment laser diode is a monolithic, single mode or multimode treatment laser diode configured to emit light at a wavelength suitable for ophthalmic treatment.

4. The apparatus according to claim 1, wherein the one or more optical elements comprise one or more lenses and/or one or more beam shapers and/or one or more beam homogenizers for adjusting a beam profile of the emitted light and to direct the treatment light beam along a predetermined direction towards the target area.

5. The apparatus according to claim 1, wherein said adapter unit comprises:
   wherein the treatment laser diode is a first monolithic, multimode treatment laser diode at a wavelength suitable for ophthalmic treatment configured to emit first laser light with a substantially linear polarization state (p1),
   a second monolithic, single mode or multimode treatment laser diode configured to emit second laser light at a wavelength suitable for ophthalmic treatment and with a substantially linear polarization state (p2) being orthogonal to p1,
   a polarization beam splitter configured to combine the emitted first and second laser light from said first monolithic, multimode treatment laser diode and from said second monolithic, single mode or multimode treatment laser diode into combined laser light, and
   one or more lenses, beam shapers or beam homogenizers for adjusting a beam profile of the emitted first and second laser light and/or of the combined laser light and to direct the combined laser light as a treatment light beam along a predetermined direction towards the target area.

6. The apparatus according to claim 1, wherein the emitted light is at a power in the range from 100 milliwatts (mW) to 3000 mW.

7. The apparatus according to claim 1, comprising a voice input unit configured to receive vocal input from an operator and to translate the vocal input into control signals to the adapter unit and and/or to output audible signals indicative of an operational parameter of the adapter unit.

8. The apparatus according to claim 7, wherein the voice input unit comprises a wireless communications interface for communication between the voice input unit and the adapter unit.

9. The apparatus according to claim 7, wherein the apparatus is configured to emit the treatment light beam as a sequence of pulses of treatment light; wherein the apparatus is configured to count a number of emitted pulses during a treatment; and wherein the voice input unit is configured to output an audible output indicative of the number of emitted pulses.

10. The apparatus according to claim 7, wherein the voice input unit is configured to receive vocal input indicative of a desired power of the emitted treatment light beam and/or indicative of a desired change in power of the emitted treatment light beam and wherein the apparatus is configured to adjust the power of the emitted treatment light beam responsive to the received vocal input.

11. The apparatus according to claim 7, wherein the apparatus is configured to emit the treatment light beam as a sequence of pulses of treatment light; wherein the voice input unit is configured to receive vocal input indicative of a desired pulse width and/or repeat interval of the emitted treatment light beam and/or indicative of a desired change in pulse width and/or repeat interval of the emitted treatment light beam and wherein the apparatus is configured to adjust the pulse width and/or repeat interval of the emitted treatment light beam responsive to the received vocal input.

12. The apparatus according to claim 1, wherein the adapter unit comprises a mounting element configured to detachably engage a tonometer mount.

13. The apparatus according to claim 1, wherein the adapter unit is movably mountable to the diagnostic instrument, moveable between an operational position and a parking position.

14. The apparatus according to claim 1, wherein the adapter unit only comprises wired input connections configured to receive electrical power and/or control signals.

15. The apparatus according to claim 1, wherein the adapter unit comprises an input for receiving electrical power, configured to receive DC power.

16. The apparatus according to claim 1, wherein the housing of the adapter unit comprises a single housing accommodating the treatment direct diode laser source, the laser controller, the pilot light source, the one or more cooling elements, and the one or more optical elements.

17. The apparatus according to claim 1, comprising a power supply unit, separate from the adapter unit and including an AC/DC converter and/or a battery.

18. The apparatus according to claim 1, comprising a user terminal separate from the adapter unit and communicatively coupled to the adapter unit, the user terminal being operable to provide a user interface, to receive user commands and to forward control commands to the adapter unit responsive to the received user commands.

19. The apparatus according to claim 1, comprising a communication unit configured to receive vocal input and/or to output an audible output.

20. An adapter unit mountable to a diagnostic instrument, the diagnostic instrument being configured to emit illumination light from an illumination output along a free-air illumination output path towards a target area for ophthalmic treatment, to receive light from the target area along a free-air viewing path and to provide a magnified view of the target area; wherein the adapter unit comprises:
  a housing detachably and rotatably mountable to the diagnostic instrument, the diagnostic instrument including a slit lamp;
  at least one treatment direct diode laser source positioned within the housing, the direct diode laser source comprising a treatment laser diode positioned within the housing and configured to emit light suitable for photothermal ophthalmic treatment at a wavelength suitable for the photothermal ophthalmic treatment in the wavelength range of 510 and 580 nanometers and with an average power of greater than 100 milliWatts;
  a pilot light source for emitting a pilot light beam of less than 5 milliWatts;
  one or more cooling elements coupled to the direct diode laser source;
  a laser controller configured to control at least the treatment laser diode;
  one or more optical elements configured to direct the emitted light from the treatment direct diode laser source as a treatment light beam and the pilot light beam along at least a portion of said free-air viewing path responsive to the housing being mounted to said diagnostic instrument; and wherein at least one of the optical elements is a dichroic mirror that is mounted to an arm that extends downward into the free-air viewing path of the diagnostic instrument responsive to the housing being mounted to said diagnostic instrument in an operational position, the dichroic mirror reflecting the treatment laser beam and pilot light beam towards the target area.

21. The apparatus according to claim 1, wherein the apparatus does not require an external fiber-optic connection between the adapter unit and an external treatment light source for conveying the light from the direct diode laser source.

22. The apparatus according to claim 1, wherein the treatment laser diode is configured to directly emit the light at a wavelength suitable for the photothermal ophthalmic treatment without the need for further components for frequency conversion and/or other lasers pumped by the treatment laser diode.

23. The apparatus according to claim 1, wherein the photothermal ophthalmic treatment is provided by causing absorption of the emitted light by structures of a subject's eye.

24. The apparatus according to claim 1, wherein the treatment laser diode emits the light at an intensity and wavelength suitable for photocoagulation and/or photothermal stimulation.

25. The apparatus according to claim 1, wherein the one or more optical elements are configured to direct the emitted light from the treatment direct diode laser as a treatment light beam towards the target area when the housing is mounted to said diagnostic instrument and without an external fiber-optic connection between the adapter unit and any external treatment light source.

26. The apparatus according to claim 1, wherein the adapter unit is a slit lamp adapter.

* * * * *